(12) United States Patent
French et al.

(10) Patent No.: US 6,307,030 B1
(45) Date of Patent: *Oct. 23, 2001

(54) ANDROGEN RECEPTOR PROTEINS, RECOMBINANT DNA MOLECULES CODING FOR SUCH, AND USE OF SUCH COMPOSITIONS

(75) Inventors: Frank S. French; Elizabeth M. Wilson; David R. Joseph, all of Chapel Hill; Dennis B. Lubahn, Durham, all of NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/182,646

(22) Filed: Apr. 15, 1988

(51) Int. Cl.⁷ .................................................. A61K 38/17

(52) U.S. Cl. ...................... 530/395; 530/350; 424/185.1

(58) Field of Search .................................. 530/350, 395; 424/185.1

(56) References Cited

U.S. PATENT DOCUMENTS

| 4,423,208 | 12/1983 | Grandics. |
| 5,614,620 | * 3/1997 | Liao et al. ........................ 536/23.5 |

FOREIGN PATENT DOCUMENTS

| WO8705049 | 8/1987 | (WO). |
| WO 89/09223 | 10/1989 | (WO). |

OTHER PUBLICATIONS

"Cloning of Human Mineralocorticoid Receptor Complementary DNA: Structural and Functional Kinship with the Gluocorticoid Receptor", Science, 237:268 (1987).
"A Critical Evaluation of the Use of Androgen Receptor Assays to Predict the Androgen Responsiveness of Prostatic Cencer", Progress in Clinical and Biological Research, Coffey et al., Editors, 239:155 (1987).
Molecular Cloning of Human and Rat Complementary DNA Encoding Androgen Receptors, Science, 240:324 (1988).
"Sequence and Expression of Human Estrogen Receptor Complementary DNA", Science, 231:1150 (1986).
"Primary Structure and Expression of a Functional Human Glucocorticoid Receptor cDNA", Science, 318:635 (1986).
"Complete Amino Acid Sequence of the Human Progesterone Receptor Deduced from Cloned cDNA", Biochem. Biophys. Res. Comm., 143:740 (1987).
Rowley et al., Biochemistry 25:6988–6995, Properties of an intermediate–sized androgen receptor: association with RNA, 1986.*
Johnson, M.P. et al., Biochemistry 26:3174–3182, A common molecular weight of the androgen receptor monomer in different target tissues, Jun. 2, 1987.*

Foekens, et al.; *Purification of the androgen receptor of sheep seminal vesicles, Chemical Abstracts*, 96:136059r; p. 106 (1982).
Trapman, *Cloning Structure and Expression of a cDNA Encoding the Human Androgen Receptor, Biochemical and Biophysical Research Communications*, 153:241–248 (1988).
Govindan, *Cloning of the human androgen receptor of cDNA, Chemical Absracts*, 109(23), p. 205 (1988).
Lubahn, *Cloning of Human Androgen Receoptor Complementary DNA and Localization to the X Chromosome; Science*, 240:327–330 (1988).
Chang, *Molecular Cloning of Human and Rat Complementary DNA Encoding Androgen Receptors, Science*, 240:324–326 (1988).
Weinberger, *The c–erb–A gene encodes a thyroid hormone receptor, Nature*, 324:641–646 (1986).
Green, *Human oestrogen receptor cDNA. sequence, expression and homology to v–erb–A, Nature*, 320:134–139 (1986).
Chang et al., *Structural analysis of complementary DNA and amino acid sequences of human and rat androgen receptors, Proceedings of the National Academy of Sciences of the USA*, 85:7211–7215 (1988).
Tilley et al., *Characterization and expression of a cDNA encoding the human androgen receptor, Proceedings of the National Academy of Sciences of the USA*, 86:327–331 (1989).
Lubahn et al., *The human androgen receptor: complementary deoxyribonucleic acid cloning, sequence analysis and gene expression in prostate, Molecular Endocrinology*, 2:1265–1275 (1988).
Foekens et al., *Purification of the androgen receptor of sheep seminal vesicles, Biochemical and Biophysical Research Communications*, 104:1279–1286(1982).
International Search Report for International Application No. PCT/US89/01548 completed Jul. 12, 1989.
Supplementary European Search Report for Application No. EP 89905317 completed May 21, 1991.
Murthy et al., Physiochemical characterization of the androgen receptor from hyperplastic human prostate. The Prostate 5:567–579, 1984.*

\* cited by examiner

*Primary Examiner*—Thomas M. Cunningham
(74) *Attorney, Agent, or Firm*—Myers Bigel Sibley & Sajovec, P.A.

(57) ABSTRACT

DNA sequences encoding human androgen receptor protein and polypeptides and proteins having substantially the same biological activity as human androgen receptor protein and the amino acid sequences of human androgen receptor protein and polypeptides and proteins having substantially the same biological activity as human androgen receptor protein are disclosed. Methods for the production and use of such compositions are also disclosed.

3 Claims, 26 Drawing Sheets

FIGURE 1C

DNA-BINDING DOMAIN

```
                      +              +  10              +          20+              +          30
hAR     (AA 567)    C L I C G D E A S G C H Y G A L T C G S C K V F F K R A A E G (100%)
hPR     (AA 603)    C L I C G D E A S G C H Y G V L T C G S C K V F F K R A M E G  (94%)
hMR     (AA 421)    C L V C G D E A S G C H Y G V V T C G S C K V F F K R A V E G  (87%)
hGR     (AA 185)    C L V C S D E A S G C H Y G V L T C G S C K V F F K R A V E G  (87%)
hER                 C A V C N D Y A S G Y H Y G V W S C E G C K A F F K R S I Q G  (55%)
cVDR                C G V C G D R A T G F H F N A M T C E G C K G F F R R S M K R  (48%)
hT3R    (AA 102)    C V V C G D K A T G Y H Y R C I T C E G C K G F F R R T I Q K  (48%)
vERBA   (AA 37)     C V V C G D K A T G Y H Y R C I T C E G C K S F F R R T I Q K  (48%)
hRAR    (AA 58)     C F V C Q D K S S G Y H Y G V S A C E G C K G F F R R S I Q K  (45%)

+              +  40              +          50              +          60+
hAR                 K Q K Y L C A S R N D C T I D K F R R K N C P S C R L R K C Y E A G M (100%)
hPR                 Q H N Y L C A G R N D C I V D K I R R K N C P A C R L R K C C Q A G M  (71%)
hMR                 Q H N Y L C A G R N D C I I D K I R R K N C P A C R L Q K C L Q A G M  (71%)
hGR                 Q H N Y L C A G R N D C I I D K I R R K N C P A C R Y R K C L Q A G M  (71%)
hER                 H N D Y M C P A T N Q C T I D K N R R K S C Q A C R L R K C Y E V G M  (63%)
cVDR                K A M F T C P F N G D C K I T D K N R R K H C Q A C R L K R C V D I G M  (40%)
hT3R                H H P S Y S C K Y E G K C V I D K V T R N Q C Q E C R F K K C I Y V G M  (40%)
vERBA   N L H P T T S C T Y D G C C I D K I T R N Q C Q L C R F K K C I S V G M  (37%)
hRAR    N L H P N M V Y T C H R D K N C I I N K V T R N R C Q Y C R L Q K C F E V G M  (43%)
```

```
          10                    30                    50
           .                     .                     .
GAGCTCTGGACAAAATTGAGCGCCTATGTGTACATGGCAAGTGTTTTTAGTGTTTGTGTG
CTCGAGACCTGTTTTAACTCGCGGATACACATGTACCGTTCACAAAAATCACAAACACAC 70                    90                   110
           .                     .                     .
TTTACCTGCTTGTCTGGGTGATTTTGCCTTTGAGAGTCTGGATGAGAAATGCATGGTTAA
AAATGGACGAACAGACCCACTAAAACGGAAACTCTCAGACCTACTCTTTACGTACCAATT 130                   150                   170
           .                     .                     .
AGGCAATTCCAGACAGGAAGAAAGGCAGAGAAGAGGGTAGAAATGACCTCTGATTCTTGG
TCCGTTAAGGTCTGTCCTTCTTTCCGTCTCTTCTCCCATCTTTACTGGAGACTAAGAACC 190                   210                   230
           .                     .                     .
GGCTGAGGGTTCCTAGAGCAAATGGCACAATGCCACGAGGCCCGATCTATCCCTATGACG
CCGACTCCCAAGGATCTCGTTTACCGTGTTACGGTGCTCCGGGCTAGATAGGGATACTGC 250                   270                   290
           .                     .                     .
GAACTCTAAGGTTTCAGCATCAGCTATCTGCTGGCTTGGTCACTGGCTTGCCTCCTCAGT
CTTGAGATTCCAAAGTCGTAGTCGATAGACGACCGAACCAGTGACCGAACGGAGGAGTCA 310                   330                   350
           .                     .                     .
TTGTAGGAGACTCTCCCACTCTCCCATCTGCGCGCTCTTATCAGTCCTGAAAAGAACCCN
AACATCCTCTGAGAGGGTGAGAGGGTAGACGCGCGAGAATAGTCAGGACTTTTCTTGGGN 370                   390                   410
           .                     .                     .
TGGCNAGCCAGGAGCNAGGTATTCNTATCGTCCTTTTCNTCCTCCTNGCCTCACCTNGTT
ACCGNTCGGTCCTCGNTCCATAAGNATAGCAGGAAAAGNAGGAGGANCGGAGTGGANCAA 430                   450                   470
           .                     .                     .
GNTTTTTAGATTGGNCTTNGNAACCAAATTGTATGCTGGCCTCCAGGAAATCTGGAGCC
CNAAAAATCTAACCNGAANCNTTGGTTTAAACATACGACCGGAGGTCCTTTAGACCTCGG 490                   510                   530
           .                     .                     .
TGGCGCCTAAACCTTGGTTTAGGAAAGCAGGAGCTATTCAGGAAGCAGGGTCCTCCAGGG
ACCGCGGATTTGGAACCAAATCCTTTCGTCCTCGATAAGTCCTTCGTCCCAGGAGGTCCC 550                   570                   590
           .                     .                     .
CTAGAGCTAGCCTCTCCTGCCCTCGCCCACGTGCGCCAGCACTTGTTTCTCCAAAGCNAC
GATCTCGATCGGAGAGGACGGGAGCGGGTGCACGCGGTCGTGAACAAAGAGGTTTCGNTG 610                   630                   650
           .                     .                     .
TAGGCAGGCGTTAGCGCGCGGTGAGGGGAGGGGAGAAAAGGAAAGGGGAGGGGAGGGAAA
ATCCGTCCGCAATCGCGCGCCACTCCCCTCCCCTCTTTTCCTTTCCCCTCCCCTCCCTTT
```

FIGURE 4A

```
        670                  690                 710
         .                    .                   .
AGGAGGTGGGAAGGCAAGGAGGCCGGCCNGGTGGGGGCGGGACCCGACTCGCANNAACTG
TCCTCCACCCTTCCGTTCCTCCGGCCGGNCCACCCCCGCCCTGGGCTGAGCGTNNTTGAC 730                  750                 770
         .                    .                   .
TTGCATTTGCTCTCCACCTCCCAGCGCCCCCTCCGAGATCCCGGGGAGCCAGCTTGCTGG
AACGTAAACGAGAGGTGGAGGGTCGCGGGGGAGGCTCTAGGGCCCCTCGGTCGAACGACC 790                  810                 830
         .                    .                   .
GAGAGCGGGAACGGTCCGGAGCAAGCCCAGAGGCAGAGGAGGCGACAGAGGGAAAAAGGG
CTCTCGCCCTTGCCAGGCCTCGTTCGGGTCTCCGTCTCCTCCGCTGTCTCCCTTTTTCCC 850                  870                 890
         .                    .                   .
CCCNAGCTAGCCGCTCCAGTGCTGTACAGNAGCCGAAGGACGCACCACGCCAGCCCCAGC
GGGNTCGATCGGCGAGGTCACGACATGTCNTCGGCTTCCTGCGTGGTGCGGTCGGGGTCG 910                  930                 950
         .                    .                   .
CCGGCTCCAGCGACAGCNAACGCCTCTTGCANGCGTTCGAAGCCGCCGCCCGGAGCTGCC
GGCCGAGGTCGCTGTCGNTTGCGGAGAACGTNCGCAAGCTTCGGCGGCGGGCCTCGACGG 970                  990                 1010
         .                    .                   .
CTTTCCTCTTCGGTGAAGTTTTTAAAAGCTGCTAAAGACTCGGAGGAAGCAAGGAAAGTG
GAAAGGAGAAGCCACTTCAAAAATTTTCGACGATTTCTGAGCCTCCTTCGTTCCTTTCAC 1030                 1050                1070
         .                    .                   .
CCTGGTAGGACTGACGGCTGCCTTTGTCCTCCTCCTCTCCACCCCGCCTCCCCCCACCCT
GGACCATCCTGACTGCCGACGGAAACAGGAGGAGGAGAGGTGGGGCGGAGGGGGGTGGGA 1090                 1110                1130
         .                    .                   .
GCCTTCCCCCCCTCCCCCGTCTTCTCTCCCGCAGCTGCCTCAGTCGGCTACTCTCAGCCA
CGGAAGGGGGGGAGGGGGCAGAAGAGAGGGCGTCGACGGAGTCAGCCGATGAGAGTCGGT 1150                 1170                1190
         .                    .                   .
ACCCCCCTCACCACCCTTCTCCCCACCCGCCCCCCCGCCCCCGTCGGCCCAGCGNTGNCA
TGGGGGGAGTGGTGGGAAGAGGGGTGGGCGGGGGGCGGGGGCAGCCGGGTCGCNACNGT 1210                 1230                1250
         .                    .                   .
GNCCGAGTTTGCAGAGAGGTAACTCCCTTTGGCTGCGAGCGGGCGAGNCTAGCTGCACAT
CNGGCTCAAACGTCTCTCCATTGAGGGAAACCGACGCTCGCCCGCTCNGATCGACGTGTA 1270                 1290                1310
         .                    .                   .
TGCAAAGAAGGCTCTTAGGAGCAGGCGACTGGGGAGCGGCTTCAGCACTGCAGCCACGAC
ACGTTTCTTCCGAGAATCCTCGTCCGCTGACCCCTCGCCGAAGTCGTGACGTCGGTGCTG
```

FIGURE 4B

```
           1330              1350                1370
            .                 .                   .
CNGCCTGGTTAGGCTGCACGCGGAGAGAACCCTCTGTTTTCCCCCACTCTCTCTCCACCT
GNCGGACCAATCCGACGTGCGCCTCTCTTGGGAGACAAAAGGGGGTGAGAGAGAGGTGGA 1390              1410                1430
            .                 .                   .
CCTCCTGCCTTCCCCACCCCGAGTGCGGAGCCAGAGATCAAAAGATGAAAAGGCAGTCAG
GGAGGACGGAAGGGGTGGGGCTCACGCCTCGGTCTCTAGTTTTCTACTTTTCCGTCAGTC 1450              1470                1490
            .                 .                   .
GTCTTCAGTAGCCAAAAAACAAAACAAACAAAAACAAAAAAGCCGAAATAAAAGAAAAAG
CAGAAGTCATCGGTTTTTGTTTTGTTTGTTTTTGTTTTTTCGGCTTTATTTTCTTTTTC 1510              1530                1550
            .                 .                   .
ATAATAACTCAGTTCTTATTTGCACCTACTTCAGTGGACACTGAATTTGGAAGGTGGAGG
TATTATTGAGTCAAGAATAAACGTGGATGAAGTCACCTGTGACTTAAACCTTCCACCTCC 1570              1590                1610
            .                 .                   .
ATTTTGTTTTTTTCTTTTAAGATCTGGGCATCTTTTGAATCTACCCTTCAAGTATTAAGA
TAAAACAAAAAAAGAAAATTCTAGACCCGTAGAAAACTTAGATGGGAAGTTCATAATTCT 1630              1650                1670
            .                 .                   .
GACAGACTGTGAGCCTAGCAGGGCAGATCTTGTCCACCGTGTGTCTTCTTCTGCACGAGA
CTGTCTGACACTCGGATCGTCCCGTCTAGAACAGGTGGCACACAGAAGAAGACGTGCTCT 1690              1710                1730
            .                 .                   .
CTTTGAGGCTGTCAGAGCGCTTTTTGCGTGGTTGCTCCCGCAAGTTTCCTTCTCTGGAGC
GAAACTCCGACAGTCTCGCGAAAAACGCACCAACGAGGGCGTTCAAAGGAAGAGACCTCG 1750              1770                1790
            .                 .                   .
TTCCCGCAGGTGGGCAGCTAGCTGCAGCGACTACCGCATCATCACAGCCTGTTGAACTCT
AAGGGCGTCCACCCGTCGATCGACGTCGCTGATGGCGTAGTAGTGTCGGACAACTTGAGA 1810              1830                1850
            .                 .                   .
TCTGAGCAAGAGAAGGGGAGGCGGGGTAAGGGAAGTAGGTGGAAGATTCAGCCAAGCTCA
AGACTCGTTCTCTTCCCCTCCGCCCCATTCCCTTCATCCACCTTCTAAGTCGGTTCGAGT 1870              1890                1910
            .                 .                   .
AGGATGGAAGTGCAGTTAGGGCTGGGAAGGGTCTACCCTCGGCCGCCGTCCAAGACCTAC
TCCTACCTTCACGTCAATCCCGACCCTTCCCAGATGGGAGCCGGCGGCAGGTTCTGGATG 1930              1950                1970
            .                 .                   .
CGAGGAGCTTTCCAGAATCTGTTCCAGAGCGTGCGCGAAGTGATCCAGAACCCGGGCCCC
GCTCCTCGAAAGGTCTTAGACAAGGTCTCGCACGCGCTTCACTAGGTCTTGGGCCCGGGG
```

FIGURE 4C

```
                    1990                    2010                    2030
                     .                       .                       .
AGGCACCCAGAGGCCGCGAGCGCAGCACCTCCCGGCGCCAGTTTGCTGCTGCTGCAGCAG
TCCGTGGGTCTCCGGCGCTCGCGTCGTGGAGGGCCGCGGTCAAACGACGACGACGTCGTC 2050                    2070                    2090
                     .                       .                       .
CAGCAGCAGCAGCAGCAGCAGCAGCAGCAGCAGCAGCAGCAGCAGCAGCAGCAGCAGCAG
GTCGTCGTCGTCGTCGTCGTCGTCGTCGTCGTCGTCGTCGTCGTCGTCGTCGTCGTCGTC 2110                    2130                    2150
                     .                       .                       .
CAGCAGCAAGAGACTAGCCCCAGGCAGCAGCAGCAGCAGCAGGGTGAGGATGGTTCTCCC
GTCGTCGTTCTCTGATCGGGGTCCGTCGTCGTCGTCGTCGTCCCACTCCTACCAAGAGGG 2170                    2190                    2210
                     .                       .                       .
CAAGCCCATCGTAGAGGCCCCACAGGCTACCTGGTCCTGGATGAGGAACAGCAACCTTCA
GTTCGGGTAGCATCTCCGGGGTGTCCGATGGACCAGGACCTACTCCTTGTCGTTGGAAGT 2230                    2250                    2270
                     .                       .                       .
CAGCCGCAGTCGGCCCTGGAGTGCCACCCCGAGAGAGGTTGCGTCCCAGAGCCTGGAGCC
GTCGGCGTCAGCCGGGACCTCACGGTGGGGCTCTCTCCAACGCAGGGTCTCGGACCTCGG 2290                    2310                    2330
                     .                       .                       .
GCCGTGGCCGCCAGCAAGGGGCTGCCGCAGCAGCTGCCAGCACCTCCGGACGAGGATGAC
CGGCACCGGCGGTCGTTCCCCGACGGCGTCGTCGACGGTCGTGGAGGCCTGCTCCTACTG 2350                    2370                    2390
                     .                       .                       .
TCAGCTGCCCCATCCACGTTGTCCCTGCTGGGCCCCACTTTCCCCGGCTTAAGCAGCTGC
AGTCGACGGGGTAGGTGCAACAGGGACGACCCGGGGTGAAAGGGGCCGAATTCGTCGACG 2410                    2430                    2450
                     .                       .                       .
TCCGCTGACCTTAAAGACATCCTGAGCGAGGCCAGCACCATGCAACTCCTTCAGCAACAG
AGGCGACTGGAATTTCTGTAGGACTCGCTCCGGTCGTGGTACGTTGAGGAAGTCGTTGTC 2470                    2490                    2510
                     .                       .                       .
CAGCAGGAAGCAGTATCCGAAGGCAGCAGCAGCGGGAGAGCGAGGGAGGCCTCGGGGGCT
GTCGTCCTTCGTCATAGGCTTCCGTCGTCGTCGCCCTCTCGCTCCTCCGGAGCCCCCGA 2530                    2550                    2570
                     .                       .                       .
CCCACTTCCTCCAAGGACAATTACTTAGGGGGCACTTCGACCATTTCTGACAACGCCAAG
GGGTGAAGGAGGTTCCTGTTAATGAATCCCCCGTGAAGCTGGTAAAGACTGTTGCGGTTC 2590                    2610                    2630
                     .                       .                       .
GAGTTGTGTAAGGCAGTGTCGGTGTCCATGGGCCTGGGTGTGGAGGCGTTGGAGCATCTG
CTCAACACATTCCGTCACAGCCACAGGTACCCGGACCCACACCTCCGCAACCTCGTAGAC
```

FIGURE 4D

```
          2650                  2670                  2690
            .                     .                     .
AGTCCAGGGGAACAGCTTCGGGGGGATTGCATGTACGCCCCACTTTTGGGAGTTCCACCC
TCAGGTCCCCTTGTCGAAGCCCCCTAACGTACATGCGGGGTGAAAACCCTCAAGGTGGG 2710                  2730                  2750
            .                     .                     .
GCTGTGCGTCCCACTCCTTGTGCCCCATTGGCCGAATGCAAAGGTTCTCTGCTAGACGAC
CGACACGCAGGGTGAGGAACACGGGGTAACCGGCTTACGTTTCCAAGAGACGATCTGCTG 2770                  2790                  2810
            .                     .                     .
AGCGCAGGCAAGAGCACTGAAGATACTGCTGAGTATTCCCCTTTCAAGGGAGGTTACACC
TCGCGTCCGTTCTCGTGACTTCTATGACGACTCATAAGGGGAAAGTTCCCTCCAATGTGG 2830                  2850                  2870
            .                     .                     .
AAAGGGCTAGAAGGCGAGAGCCTAGGCTGCTCTGGCAGCGCTGCAGCAGGGAGCTCCGGG
TTTCCCGATCTTCCGCTCTCGGATCCGACGAGACCGTCGCGACGTCGTCCCTCGAGGCCC 2890                  2910                  2930
            .                     .                     .
ACACTTGAACTGCCGTCTACCCTGTCTCTCTACAAGTCCGGAGCACTGGACGAGGCAGCT
TGTGAACTTGACGGCAGATGGGACAGAGAGATGTTCAGGCCTCGTGACCTGCTCCGTCGA 2950                  2970                  2990
            .                     .                     .
GCGTACCAGAGTCGCGACTACTACAACTTTCCACTGGCTCTGGCCGGACCGCCGCCCCCT
CGCATGGTCTCAGCGCTGATGATGTTGAAAGGTGACCGAGACCGGCCTGGCGGCGGGGGA 3010                  3030                  3050
            .                     .                     .
CCGCCGCCTCCCCATCCCCACGCTCGCATCAAGCTGGAGAACCCGCTGGACTACGGCAGC
GGCGGCGGAGGGGTAGGGGTGCGAGCGTAGTTCGACCTCTTGGGCGACCTGATGCCGTCG 3070                  3090                  3110
            .                     .                     .
GCCTGGGCGGCTGCGGCGGCGCAGTGCCGCTATGGGGACCTGGCGAGCCTGCATGGCGCG
CGGACCCGCCGACGCCGCCGCGTCACGGCGATACCCCTGGACCGCTCGGACGTACCGCGC 3130                  3150                  3170
            .                     .                     .
GGTGCAGCGGGACCCGGTTCTGGGTCACCCTCAGCCGCCGCTTCCTCATCCTGGCACACT
CCACGTCGCCCTGGGCCAAGACCCAGTGGGAGTCGGCGGCGAAGGAGTAGGACCGTGTGA 3190                  3210                  3230
            .                     .                     .
CTCTTCACAGCCGAAGAAGGCCAGTTGTATGGACCGTGTGGTGGTGGTGGGGGTGGTGGC
GAGAAGTGTCGGCTTCTTCCGGTCAACATACCTGGCACACCACCACCACCCCCACCACCG 3250                  3270                  3290
            .                     .                     .
GGCGGCGGCGGCGGCGGCGGCGGCGGCGGCGGCGGCGGCGGCGGCGGCGGCGAGGCGGGA
CCGCCGCCGCCGCCGCCGCCGCCGCCGCCGCCGCCGCCGCCGCCGCCGCCGCTCCGCCCT
```

FIGURE 4E

```
              3310                  3330                  3350
               .                     .                     .
               .                     .                     .
GCTGTAGCCCCCTACGGCTACACTCGGCCCCCTCAGGGGCTGGCGGGCCAGGAAAGCGAC
CGACATCGGGGGATGCCGATGTGAGCCGGGGGAGTCCCCGACCGCCCGGTCCTTTCGCTG 3370                  3390                  3410
               .                     .                     .
               .                     .                     .
TTCACCGCACCTGATGTGTGGTACCCTGGCGGCATGGTGAGCAGAGTGCCCTATCCCAGT
AAGTGGCGTGGACTACACACCATGGGACCGCCGTACCACTCGTCTCACGGGATAGGGTCA 3430                  3450                  3470
               .                     .                     .
               .                     .                     .
CCCACTTGTGTCAAAAGCGAAATGGGCCCCTGGATGGATAGCTACTCCGGACCTTACGGG
GGGTGAACACAGTTTTCGCTTTACCCGGGGACCTACCTATCGATGAGGCCTGGAATGCCC 3490                  3510                  3530
               .                     .                     .
               .                     .                     .
GACATGCGTTTGGAGACTGCCAGGGACCATGTTTTGCCCATTGACTATTACTTTCCACCC
CTGTACGCAAACCTCTGACGGTCCCTGGTACAAAACGGGTAACTGATAATGAAAGGTGGG 3550                  3570                  3590
               .                     .                     .
               .                     .                     .
CAGAAGACCTGCCTGATCTGTGGAGATGAAGCTTCTGGGTGTCACTATGGAGCTCTCACA
GTCTTCTGGACGGACTAGACACCTCTACTTCGAAGACCCACAGTGATACCTCGAGAGTGT 3610                  3630                  3650
               .                     .                     .
               .                     .                     .
TGTGGAAGCTGCAAGGTCTTCTTCAAAAGAGCCGCTGAAGGGAAACAGAAGTACCTGTGC
ACACCTTCGACGTTCCAGAAGAAGTTTTCTCGGCGACTTCCCTTTGTCTTCATGGACACG 3670                  3690                  3710
               .                     .                     .
               .                     .                     .
GCCAGCAGAAATGATTGCACTATTGATAAATTCCGAAGGAAAAATTGTCCATCTTGTCGT
CGGTCGTCTTTACTAACGTGATAACTATTTAAGGCTTCCTTTTTAACAGGTAGAACAGCA 3730                  3750                  3770
               .                     .                     .
               .                     .                     .
CTTCGGAAATGTTATGAAGCAGGGATGACTCTGGGAGCCCGGAAGCTGAAGAAACTTGGT
GAAGCCTTTACAATACTTCGTCCCTACTGAGACCCTCGGGCCTTCGACTTCTTTGAACCA 3790                  3810                  3830
               .                     .                     .
               .                     .                     .
AATCTGAAACTACAGGAGGAAGGAGAGGCTTCCAGCACCACCAGCCCCACTGAGGAGACA
TTAGACTTTGATGTCCTCCTTCCTCTCCGAAGGTCGTGGTGGTCGGGGTGACTCCTCTGT 3850                  3870                  3890
               .                     .                     .
               .                     .                     .
ACCCAGAAGCTGACAGTGTCACACATTGAAGGCTATGAATGTCAGCCCATCTTTCTGAAT
TGGGTCTTCGACTGTCACAGTGTGTAACTTCCGATACTTACAGTCGGGTAGAAAGACTTA 3910                  3930                  3950
               .                     .                     .
               .                     .                     .
GTCCTGGAAGCCATTGAGCCAGGTGTAGTGTGTGCTGGACACGACAACAACCAGCCCGAC
CAGGACCTTCGGTAACTCGGTCCACATCACACACGACCTGTGCTGTTGTTGGTCGGGCTG
```

FIGURE 4F

```
                    3970                      3990                           4010
                      .                         .                              .
TCCTTTGCAGCCTTGCTCTCTAGCCTCAATGAACTGGGAGAGAGACAGCTTGTACACGTG
AGGAAACGTCGGAACGAGAGATCGGAGTTACTTGACCCTCTCTCTGTCGAACATGTGCAC 4030                      4050                           4070
                      .                         .                              .
GTCAAGTGGGCCAAGGCCTTGCCTGGCTTCCGCAACTTACACGTGGACGACCAGATGGCT
CAGTTCACCCGGTTCCGGAACGGACCGAAGGCGTTGAATGTGCACCTGCTGGTCTACCGA 4090                      4110                           4130
                      .                         .                              .
GTCATTCAGTACTCCTGGATGGGGCTCATGGTGTTTGCCATGGGCTGGCGATCCTTCACC
CAGTAAGTCATGAGGACCTACCCCGAGTACCACAAACGGTACCCGACCGCTAGGAAGTGG 4150                      4170                           4190
                      .                         .                              .
AATGTCAACTCCAGGATGCTCTACTTCGCCCCTGATCTGGTTTTCAATGAGTACCGCATG
TTACAGTTGAGGTCCTACGAGATGAAGCGGGGACTAGACCAAAAGTTACTCATGGCGTAC 4210                      4230                           4250
                      .                         .                              .
CACAAGTCCCGGATGTACAGCCAGTGTGTCCGAATGAGGCACCTCTCTCAAGAGTTTGGA
GTGTTCAGGGCCTACATGTCGGTCACACAGGCTTACTCCGTGGAGAGAGTTCTCAAACCT 4270                      4290                           4310
                      .                         .                              .
TGGCTCCAAATCACCCCCCAGGAATTCCTGTGCATGAAAGCACTGCTACTCTTCAGCATT
ACCGAGGTTTAGTGGGGGGTCCTTAAGGACACGTACTTTCGTGACGATGAGAAGTCGTAA 4330                      4350                           4370
                      .                         .                              .
ATTCCAGTGGATGGGCTGAAAAATCAAAAATTCTTTGATGAACTTCGAATGAACTACATC
TAAGGTCACCTACCCGACTTTTTAGTTTTTAAGAAACTACTTGAAGCTTACTTGATGTAG 4390                      4410                           4430
                      .                         .                              .
AAGGAACTCGATCGTATCATTGCATGCAAAAGAAAAAATCCCACATCCTGCTCAAGACGC
TTCCTTGAGCTAGCATAGTAACGTACGTTTTCTTTTTAGGGTGTAGGACGAGTTCTGCG 4450                      4470                           4490
                      .                         .                              .
TTCTACCAGCTCACCAAGCTCCTGGACTCCGTGCAGCCTATTGCGAGAGAGCTGCATCAG
AAGATGGTCGAGTGGTTCGAGGACCTGAGGCACGTCGGATAACGCTCTCTCGACGTAGTC 4510                      4530                           4550
                      .                         .                              .
TTCACTTTTGACCTGCTAATCAAGTCACACATGGTGAGCGTGGACTTTCCGGAAATGATG
AAGTGAAAACTGGACGATTAGTTCAGTGTGTACCACTCGCACCTGAAAGGCCTTTACTAC 4570                      4590                           4610
                      .                         .                              .
GCAGAGATCATCTCTGTGCAAGTGCCCAAGATCCTTTCTGGGAAAGTCAAGCCCATCTAT
CGTCTCTAGTAGAGACACGTTCACGGGTTCTAGGAAAGACCCTTTCAGTTCGGGTAGATA
```

FIGURE 4G

```
                4630                    4650                    4670
                 .                       .                       .
                 .                       .                       .
TTCCACACCCAGTGAAGCATTGGAAACCCTATTTCCCCACCCCAGCTCATGCCCCCTTTC
AAGGTGTGGGTCACTTCGTAACCTTTGGGATAAAGGGGTGGGGTCGAGTACGGGGGAAAG 4690                    4710                    4730
                 .                       .                       .
                 .                       .                       .
AGATGTCTTCTGCCTGTTATAACTCTGCACTACTCCTCTGCAGTGCCTTGGGGAATTTCC
TCTACAGAAGACGGACAATATTGAGACGTGATGAGGAGACGTCACGGAACCCCTTAAAGG 4750                    4770                    4790
                 .                       .                       .
                 .                       .                       .
TCTATTGATGTACAGTCTGTCATGAACATGTTCCTGAATTCTATTTGCTGGGCTTTTTTT
AGATAACTACATGTCAGACAGTACTTGTACAAGGACTTAAGATAAACGACCCGAAAAAAA 4810                    4830                    4850
                 .                       .                       .
                 .                       .                       .
TTCTCTTTCTCTCCTTTCTTTTTCTTCTTCCCTCCCTATCTAACCCTCCCATGGCACCTT
AAGAGAAAGAGAGGAAAGAAAAGAAGAAGGGAGGGATAGATTGGGAGGGTACCGTGGAA 4870                    4890                    4910
                 .                       .                       .
                 .                       .                       .
CAGACTTTGCTTCCCATTGTGGCTCCTATCTGTGTTTTGAATGGTGTTGTATGCCTTTAA
GTCTGAAACGAAGGGTAACACCGAGGATAGACACAAAACTTACCACAACATACGGAAATT 4930                    4950                    4970
                 .                       .                       .
                 .                       .                       .
ATCTGTGATGATCCTCATATGGCCCAGTGTCAAGTTGTGCTTGTTTACAGCACTACTCTG
TAGACACTACTAGGAGTATACCGGGTCACAGTTCAACACGAACAAATGTCGTGATGAGAC 4990                    5010                    5030
                 .                       .                       .
                 .                       .                       .
TGCCAGCCACACAAACGTTTACTTATCTTATGCCACGGGAAGTTTAGAGAGCTAAGATTA
ACGGTCGGTGTGTTTGCAAATGAATAGAATACGGTGCCCTTCAAATCTCTCGATTCTAAT 5050                    5070
                 .                       .
                 .                       .
TCTGGGGAAATCAAAACAAAAACAAGCAAACAAAAAAAAA
AGACCCCTTTAGTTTTGTTTTTGTTCGTTTGTTTTTTTTT
```

FIGURE 4H

```
   1 GAGCTCTGGACAAAATTGAGCGCCTATGTGTACATGGCAAGTGTTTTAGTGTTTGTGTG
  61 TTTACCTGCTTGTCTGGGTGATTTTGCCTTTGAGAGTCTGGATGAGAAATGCATGGTTAA
 121 AGGCAATTCCAGACAGGAAGAAAGGCAGAGAAGAGGGTAGAAATGACCTCTGATTCTTGG
 181 GGCTGAGGGTTCCTAGAGCAAATGGCACAATGCCACGAGGCCCGATCTATCCCTATGACG
 241 GAACTCTAAGGTTTCAGCATCAGCTATCTGCTGGCTTGGTCACTGGCTTGCCTCCTCAGT
 301 TTGTAGGAGACTCTCCCACTCTCCCATCTGCGCGCTCTTATCAGTCCTGAAAAGAACCCN
 361 TGGCNAGCCAGGAGCNAGGTATTCNTATCGTCCTTTTCNTCCTCCTNGCCTCACCTNGTT
 421 GNTTTTTAGATTGGNCTTNGNAACCAAATTTGTATGCTGGCCTCCAGGAAATCTGGAGCC
 481 TGGCGCCTAAACCTTGGTTTAGGAAAGCAGGAGCTATTCAGGAAGCAGGGTCCTCCAGGG
 541 CTAGAGCTAGCCTCTCCTGCCCTCGCCCACGTGCGCCAGCACTTGTTTCTCCAAAGCNAC
 601 TAGGCAGGCGTTAGCGCGCGGTGAGGGGAGGGGAGAAAAGGAAAGGGGAGGGGAGGGAAA
 661 AGGAGGTGGGAAGGCAAGGAGGCCGGCCNGGTGGGGCGGGACCCGACTCGCANNAACTG
 721 TTGCATTTGCTCTCCACCTCCCAGCGCCCCCTCCGAGATCCCGGGGAGCCAGCTTGCTGG
 781 GAGAGCGGGAACGGTCCGGAGCAAGCCCAGAGGCAGAGGAGGCGACAGAGGGAAAAGGG
 841 CCCNAGCTAGCCGCTCCAGTGCTGTACAGNAGCCGAAGGACGCACCACGCCAGCCCCAGC
 901 CCGGCTCCAGCGACAGCNAACGCCTCTTGCANGCGTTCGAAGCCGCCGCCCGGAGCTGCC
 961 CTTTCCTCTTCGGTGAAGTTTTTAAAAGCTGCTAAAGACTCGGAGGAAGCAAGGAAAGTG
1021 CCTGGTAGGACTGACGGCTGCCTTTGTCCTCCTCCTCTCCACCCCGCCTCCCCCCACCCT
```

FIGURE 5A

```
1081 GCCTTCCCCCCCTCCCCCGTCTTCTCTCCCGCAGCTGCCTCAGTCGGCTACTCTCAGCCA

1141 ACCCCCCTCACCACCCTTCTCCCCACCCGCCCCCCCGCCCCCGTCGGCCCAGCGNTGNCA

1201 GNCCGAGTTTGCAGAGAGGTAACTCCCTTTGGCTGCGAGCGGGCGAGNCTAGCTGCACAT

1261 TGCAAAGAAGGCTCTTAGGAGCAGGCGACTGGGGAGCGGCTTCAGCACTGCAGCCACGAC

1321 CNGCCTGGTTAGGCTGCACGCGGAGAGAACCCTCTGTTTTCCCCACTCTCTCTCCACCT

1381 CCTCCTGCCTTCCCCACCCCGAGTGCGGAGCCAGAGATCAAAAGATGAAAAGGCAGTCAG

1441 GTCTTCAGTAGCCAAAAAACAAAACAAACAAAAACAAAAAAGCCGAAATAAAAGAAAAAG

1501 ATAATAACTCAGTTCTTATTTGCACCTACTTCAGTGGACACTGAATTTGGAAGGTGGAGG

1561 ATTTTGTTTTTTTCTTTTAAGATCTGGGCATCTTTTGAATCTACCCTTCAAGTATTAAGA

1621 GACAGACTGTGAGCCTAGCAGGGCAGATCTTGTCCACCGTGTGTCTTCTTCTGCACGAGA

1681 CTTTGAGGCTGTCAGAGCGCTTTTTGCGTGGTTGCTCCCGCAAGTTTCCTTCTCTGGAGC

1741 TTCCCGCAGGTGGGCAGCTAGCTGCAGCGACTACCGCATCATCACAGCCTGTTGAACTCT

1801 TCTGAGCAAGAGAAGGGGAGGCGGGGTAAGGGAAGTAGGTGGAAGATTCAGCCAAGCTCA

1861 AGGATGGAAGTGCAGTTAGGGCTGGGAAGGGTCTACCCTCGGCCGCCGTCCAAGACCTAC
       MetGluValGlnLeuGlyLeuGlyArgValTyrProArgProProSerLysThrTyr

1921 CGAGGAGCTTTCCAGAATCTGTTCCAGAGCGTGCGCGAAGTGATCCAGAACCCGGGCCCC
     ArgGlyAlaPheGlnAsnLeuPheGlnSerValArgGluValIleGlnAsnProGlyPro

1981 AGGCACCCAGAGGCCGCGAGCGCAGCACCTCCCGGCGCCAGTTTGCTGCTGCTGCAGCAG
     ArgHisProGluAlaAlaSerAlaAlaProProGlyAlaSerLeuLeuLeuLeuGlnGln

2041 CAGCAGCAGCAGCAGCAGCAGCAGCAGCAGCAGCAGCAGCAGCAGCAGCAGCAGCAGCAG
     GlnGlnGlnGlnGlnGlnGlnGlnGlnGlnGlnGlnGlnGlnGlnGlnGlnGlnGlnGln
```

FIGURE 5B

```
2101 CAGCAGCAAGAGACTAGCCCCAGGCAGCAGCAGCAGCAGCAGGGTGAGGATGGTTCTCCC
     GlnGlnGlnGluThrSerProArgGlnGlnGlnGlnGlnGlyGluAspGlySerPro

2161 CAAGCCCATCGTAGAGGCCCCACAGGCTACCTGGTCCTGGATGAGGAACAGCAACCTTCA
     GlnAlaHisArgArgGlyProThrGlyTyrLeuValLeuAspGluGluGlnGlnProSer

2221 CAGCCGCAGTCGGCCCTGGAGTGCCACCCCGAGAGAGGTTGCGTCCCAGAGCCTGGAGCC
     GlnProGlnSerAlaLeuGluCysHisProGluArgGlyCysValProGluProGlyAla

2281 GCCGTGGCCGCCAGCAAGGGGCTGCCGCAGCAGCTGCCAGCACCTCCGGACGAGGATGAC
     AlaValAlaAlaSerLysGlyLeuProGlnGlnLeuProAlaProProAspGluAspAsp

2341 TCAGCTGCCCCATCCACGTTGTCCCTGCTGGGCCCCACTTTCCCCGGCTTAAGCAGCTGC
     SerAlaAlaProSerThrLeuSerLeuLeuGlyProThrPheProGlyLeuSerSerCys

2401 TCCGCTGACCTTAAAGACATCCTGAGCGAGGCCAGCACCATGCAACTCCTTCAGCAACAG
     SerAlaAspLeuLysAspIleLeuSerGluAlaSerThrMetGlnLeuLeuGlnGlnGln

2461 CAGCAGGAAGCAGTATCCGAAGGCAGCAGCAGCGGGAGAGCGAGGGAGGCCTCGGGGGCT
     GlnGlnGluAlaValSerGluGlySerSerSerGlyArgAlaArgGluAlaSerGlyAla

2521 CCCACTTCCTCCAAGGACAATTACTTAGGGGGCACTTCGACCATTTCTGACAACGCCAAG
     ProThrSerSerLysAspAsnTyrLeuGlyGlyThrSerThrIleSerAspAsnAlaLys

2581 GAGTTGTGTAAGGCAGTGTCGGTGTCCATGGGCCTGGGTGTGGAGGCGTTGGAGCATCTG
     GluLeuCysLysAlaValSerValSerMetGlyLeuGlyValGluAlaLeuGluHisLeu

2641 AGTCCAGGGGAACAGCTTCGGGGGGATTGCATGTACGCCCCACTTTTGGGAGTTCCACCC
     SerProGlyGluGlnLeuArgGlyAspCysMetTyrAlaProLeuLeuGlyValProPro

2701 GCTGTGCGTCCCACTCCTTGTGCCCCATTGGCCGAATGCAAAGGTTCTCTGCTAGACGAC
     AlaValArgProThrProCysAlaProLeuAlaGluCysLysGlySerLeuLeuAspAsp

2761 AGCGCAGGCAAGAGCACTGAAGATACTGCTGAGTATTCCCCTTTCAAGGGAGGTTACACC
     SerAlaGlyLysSerThrGluAspThrAlaGluTyrSerProPheLysGlyGlyTyrThr

2821 AAAGGGCTAGAAGGCGAGAGCCTAGGCTGCTCTGGCAGCGCTGCAGCAGGGAGCTCCGGG
     LysGlyLeuGluGlyGluSerLeuGlyCysSerGlySerAlaAlaAlaGlySerSerGly
```

FIGURE 5C

```
2881  ACACTTGAACTGCCGTCTACCCTGTCTCTCTACAAGTCCGGAGCACTGGACGAGGCAGCT
      ThrLeuGluLeuProSerThrLeuSerLeuTyrLysSerGlyAlaLeuAspGluAlaAla

2941  GCGTACCAGAGTCGCGACTACTACAACTTTCCACTGGCTCTGGCCGGACCGCCGCCCCCT
      AlaTyrGlnSerArgAspTyrTyrAsnPheProLeuAlaLeuAlaGlyProProProPro

3001  CCGCCGCCTCCCCATCCCCACGCTCGCATCAAGCTGGAGAACCCGCTGGACTACGGCAGC
      ProProProProHisProHisAlaArgIleLysLeuGluAsnProLeuAspTyrGlySer

3061  GCCTGGGCGGCTGCGGCGGCGCAGTGCCGCTATGGGGACCTGGCGAGCCTGCATGGCGCG
      AlaTrpAlaAlaAlaAlaAlaGlnCysArgTyrGlyAspLeuAlaSerLeuHisGlyAla

3121  GGTGCAGCGGGACCCGGTTCTGGGTCACCCTCAGCCGCCGCTTCCTCATCCTGGCACACT
      GlyAlaAlaGlyProGlySerGlySerProSerAlaAlaAlaSerSerSerTrpHisThr

3181  CTCTTCACAGCCGAAGAAGGCCAGTTGTATGGACCGTGTGGTGGTGGTGGGGGTGGTGGC
      LeuPheThrAlaGluGluGlyGlnLeuTyrGlyProCysGlyGlyGlyGlyGlyGlyGly

3241  GGCGGCGGCGGCGGCGGCGGCGGCGGCGGCGGCGGCGGCGGCGGCGGCGAGGCGGGA
      GlyGlyGlyGlyGlyGlyGlyGlyGlyGlyGlyGlyGlyGlyGlyGlyGluAlaGly

3301  GCTGTAGCCCCCTACGGCTACACTCGGCCCCCTCAGGGGCTGGCGGGCCAGGAAAGCGAC
      AlaValAlaProTyrGlyTyrThrArgProProGlnGlyLeuAlaGlyGlnGluSerAsp

3361  TTCACCGCACCTGATGTGTGGTACCCTGGCGGCATGGTGAGCAGAGTGCCCTATCCCAGT
      PheThrAlaProAspValTrpTyrProGlyGlyMetValSerArgValProTyrProSer

3421  CCCACTTGTGTCAAAAGCGAAATGGGCCCCTGGATGGATAGCTACTCCGGACCTTACGGG
      ProThrCysValLysSerGluMetGlyProTrpMetAspSerTyrSerGlyProTyrGly

3481  GACATGCGTTTGGAGACTGCCAGGGACCATGTTTTGCCCATTGACTATTACTTTCCACCC
      AspMetArgLeuGluThrAlaArgAspHisValLeuProIleAspTyrTyrPheProPro

3541  CAGAAGACCTGCCTGATCTGTGGAGATGAAGCTTCTGGGTGTCACTATGGAGCTCTCACA
      GlnLysThrCysLeuIleCysGlyAspGluAlaSerGlyCysHisTyrGlyAlaLeuThr

3601  TGTGGAAGCTGCAAGGTCTTCTTCAAAAGAGCCGCTGAAGGGAAACAGAAGTACCTGTGC
      CysGlySerCysLysValPhePheLysArgAlaAlaGluGlyLysGlnLysTyrLeuCys

3661  GCCAGCAGAAATGATTGCACTATTGATAAATTCCGAAGGAAAAATTGTCCATCTTGTCGT
      AlaSerArgAsnAspCysThrIleAspLysPheArgArgLysAsnCysProSerCysArg
```

FIGURE 5D

```
3721  CTTCGGAAATGTTATGAAGCAGGGATGACTCTGGGAGCCCGGAAGCTGAAGAAACTTGGT
      LeuArgLysCysTyrGluAlaGlyMetThrLeuGlyAlaArgLysLeuLysLysLeuGly

3781  AATCTGAAACTACAGGAGGAAGGAGAGGCTTCCAGCACCACCAGCCCCACTGAGGAGACA
      AsnLeuLysLeuGlnGluGluGlyGluAlaSerSerThrThrSerProThrGluGluThr

3841  ACCCAGAAGCTGACAGTGTCACACATTGAAGGCTATGAATGTCAGCCCATCTTTCTGAAT
      ThrGlnLysLeuThrValSerHisIleGluGlyTyrGluCysGlnProIlePheLeuAsn

3901  GTCCTGGAAGCCATTGAGCCAGGTGTAGTGTGTGCTGGACACGACAACAACCAGCCCGAC
      ValLeuGluAlaIleGluProGlyValValCysAlaGlyHisAspAsnAsnGlnProAsp

3961  TCCTTTGCAGCCTTGCTCTCTAGCCTCAATGAACTGGGAGAGAGACAGCTTGTACACGTG
      SerPheAlaAlaLeuLeuSerSerLeuAsnGluLeuGlyGluArgGlnLeuValHisVal

4021  GTCAAGTGGGCCAAGGCCTTGCCTGGCTTCCGCAACTTACACGTGGACGACCAGATGGCT
      ValLysTrpAlaLysAlaLeuProGlyPheArgAsnLeuHisValAspAspGlnMetAla

4081  GTCATTCAGTACTCCTGGATGGGGCTCATGGTGTTTGCCATGGGCTGGCGATCCTTCACC
      ValIleGlnTyrSerTrpMetGlyLeuMetValPheAlaMetGlyTrpArgSerPheThr

4141  AATGTCAACTCCAGGATGCTCTACTTCGCCCCTGATCTGGTTTTCAATGAGTACCGCATG
      AsnValAsnSerArgMetLeuTyrPheAlaProAspLeuValPheAsnGluTyrArgMet

4201  CACAAGTCCCGGATGTACAGCCAGTGTGTCCGAATGAGGCACCTCTCTCAAGAGTTTGGA
      HisLysSerArgMetTyrSerGlnCysValArgMetArgHisLeuSerGlnGluPheGly

4261  TGGCTCCAAATCACCCCCCAGGAATTCCTGTGCATGAAAGCACTGCTACTCTTCAGCATT
      TrpLeuGlnIleThrProGlnGluPheLeuCysMetLysAlaLeuLeuLeuPheSerIle

4321  ATTCCAGTGGATGGGCTGAAAAATCAAAAATTCTTTGATGAACTTCGAATGAACTACATC
      IleProValAspGlyLeuLysAsnGlnLysPhePheAspGluLeuArgMetAsnTyrIle

4381  AAGGAACTCGATCGTATCATTGCATGCAAAAGAAAAAATCCCACATCCTGCTCAAGACGC
      LysGluLeuAspArgIleIleAlaCysLysArgLysAsnProThrSerCysSerArgArg

4441  TTCTACCAGCTCACCAAGCTCCTGGACTCCGTGCAGCCTATTGCGAGAGAGCTGCATCAG
      PheTyrGlnLeuThrLysLeuLeuAspSerValGlnProIleAlaArgGluLeuHisGln
```

FIGURE 5E

```
4501 TTCACTTTTGACCTGCTAATCAAGTCACACATGGTGAGCGTGGACTTTCCGGAAATGATG
     PheThrPheAspLeuLeuIleLysSerHisMetValSerValAspPheProGluMetMet

4561 GCAGAGATCATCTCTGTGCAAGTGCCCAAGATCCTTTCTGGGAAAGTCAAGCCCATCTAT
     AlaGluIleIleSerValGlnValProLysIleLeuSerGlyLysValLysProIleTyr

4621 TTCCACACCCAGTGAAGCATTGGAAACCCTATTTCCCCACCCCAGCTCATGCCCCCTTTC
     PheHisThrGlnEnd

4681 AGATGTCTTCTGCCTGTTATAACTCTGCACTACTCCTCTGCAGTGCCTTGGGGAATTTCC

4741 TCTATTGATGTACAGTCTGTCATGAACATGTTCCTGAATTCTATTTGCTGGGCTTTTTTT

4801 TTCTCTTTCTCTCCTTTCTTTTTCTTCTTCCCTCCCTATCTAACCCTCCCATGGCACCTT

4861 CAGACTTTGCTTCCCATTGTGGCTCCTATCTGTGTTTTGAATGGTGTTGTATGCCTTTAA

4921 ATCTGTGATGATCCTCATATGGCCCAGTGTCAAGTTGTGCTTGTTTACAGCACTACTCTG

4981 TGCCAGCCACACAAACGTTTACTTATCTTATGCCACGGGAAGTTTAGAGAGCTAAGATTA

5041 TCTGGGGAAATCAAAACAAAAACAAGCAAACAAAAAAAAA 5082
```

FIGURE 5F

| | |
|---|---|
| AATTCGGGAAGGATCGAGCAAACCAGGAAAGTAAGGATGGAGATCCTAGGAGAGTGTCCA | 60 |
| TGCCTCGAAAGGAGCCCACCAAAGATGAACTGTTGCATTTGCTTTCCACCTCCCAGCGCC | 120 |
| CCCTCGGAGATCCCTAGGAGCCAGCCTGCTGGGAGAACCAGAGGGTCCGGAGCAAACCTG | 180 |
| GAGGCTGAGAGGGCATCAGAGGGGAAAAGACTGAGTTAGCCACTCCAGTGCCATACAGAA | 240 |
| GCTTAAGGGACATACCACGCCAGCCCCAGCCCAGCGACAGCCAACGCCTGTTGCAGAGCG | 300 |
| GCGGCTTCGAAGCCGCCGCCCAGAAGCTGCCCTTTCCTCTTCGGTGAAGTTTCTAAAAGC | 360 |
| TGCGGGAGACTCGGAGGAAGCGAAGAAAGTGTCCGGTAGGACTACGACTGCCTTTGTCCT | 420 |
| CCTCCCTCCTACCCCTACCCCTCCTGGGTCCCCTCTCCCTGAGCGGACTAGGCAGGCTTC | 480 |
| CTGGCCAGCCCTCTCCCCTACACCACCAGCTCTGCCAGCCAGTTTGCACAGAGGTAACTC | 540 |
| CCTTTGGCTGAAAGCAGACGAGCTTGTTGCCCATTGGAAGGGAGGCTTTTGGGAGCCCAG | 600 |
| AGACTGAGGAGCAACAGCACGCTGGAGAGTCCCTGATTCCAGGTTCTCCCCCCTGCACCT | 660 |
| CCTACTGCCCGCCCCTCACCCTGTGTGTGCAGCTAGAATTGAAAAGATGAAAAGACAGTT | 720 |
| GGGGCTTCAGTAGTCGAAAGCAAAACAAAAGCAAAAGAAAACAAAAAGAAAATAGCCCA | 780 |
| GTTCTTATTTGCACCTGCTTCAGTGGACATTGACTTTGGAAGGCAGAGAATTTTCCTTCC | 840 |
| CCCCAGTCAAGCTTTGAGCATCTTTTAATCTGTTCTTCAAGTATTTAGGGACAAACTGTG | 900 |

FIGURE 6A

```
AAACTAGCAGGGCAGATCCTGTCTAGCGCGTGCCTTCCTTTACAGGAGACTTTGAGGCTA  960

TCTGGGCGCTCCCCCCCCTCCCTGCAAGTTTTCTTCCCTGGAGCTTCCCGCAGGTGGGCA 1020

GCTAGCTGCAGATACTACATCATCAGTCAGTAGAACTCTTCAGAGCAAGAGACGAGGAGG 1080

CAGGATAAGGGAATTCGGTGGAAGCTAGAGACAAGCTAAAGGATGGAGGTGCAGTTAGGG 1140
                                        MetGluValGlnLeuGly

CTGGGAAGGGTCTACCCACGGCCCCCGTCCAAGACCTATCGAGGAGCGTTCCAGAATCTG 1200
LeuGlyArgValTyrProArgProProSerlysThrTyrArgGlyAlaPheGlnAsnLeu TTCCAGAGCGTGCGCGAAGCGATCCAGAACCCGGGCCCCAGGCACCCTGAGGCCGCTAGC 1260
PheGlnSerValArgGluAlaIleGlnAsnProGlyProArgHisProGluAlaAlaSer ATAGCACCTCCCGGTGCCTGTTTACAGCAGCGGCAGGAGACTAGCCCCCGGCGGCGGCGG 1320
IleAlaProProGlyAlaCysLeuGlnGlnArgGlnGluThrSerProArgArgArgArg CGGCAGCAGCACCCTGAGGATGGCTCTCCTCAAGCCCACATCAGAGGCACCACAGGCTAC 1380
ArgGlnGlnHisProGluAspGlySerProGlnAlaHisIleArgGlyThrThrGlyTyr CTGGCCCTGGAGGAGGAACAGCAGCCTTCACAGCAGCAGTCAGCCTCCGAGGGCCACCCT 1440
LeuAlaLeuGluGluGluGlnGlnProSerGlnGlnGlnSerAlaSerGluGlyHisPro GAGAGCGGCTGCCTCCCGGAGCCTGGAGCTGCCACGGCTCCTGGCAAGGGGCTGCCGCAG 1500
GluSerGlyCysLeuProGluProGlyAlaAlaThrAlaProGlyLysGlyLeuProGln CAGCCACCAGCTCCTCCAGATCAGGATGACTCAGCTGCCCCATCCACGTTGTCCCTACTG 1560
GlnProProAlaProProAspGlnAspAspSerAlaAlaProSerThrLeuSerLeuLeu GGCCCCACTTTCCCAGGCTTAAGCAGCTGCTCCGCAGACATTAAAGACATCCTGAGCGAG 1620
GlyProThrPheProGlyLeuSerSerCysSerAlaAspIleLysAspIleLeuSerGlu GCCGGCACCATGCAACTTCTTCAGCAGCAGCAGCAACAGCAACAGCAGCAGCAGCAGCAG 1680
AlaGlyThrMetGlnLeuLeuGlnGlnGlnGlnGlnGlnGlnGlnGlnGlnGlnGlnGln CAGCAGCAGCAGCAGCAACAGCAGCAGGAGGTAATATCCGAAGGCAGCAGCAGCGTGAGA 1740
GlnGlnGlnGlnGlnGlnGlnGlnGluValIleSerGluGlySerSerSerValArg GCAAGGGAGGCCACTGGGGCTCCCTCTTCCTCCAAGGATAGTTACCTAGGGGGCAATTCG 1800
AlaArgGluAlaThrGlyAlaProSerSerSerLysAspSerTyrLeuGlyGlyAsnSer
```

FIGURE 6B

```
ACCATATCTGACAGTGCCAAGGAGTTGTGTAAAGCAGTGTCTGTGTCCATGGGGTTGGGT 1860
ThrIleSerAspSerAlaLysGluLeuCysLysAlaValSerValSerMetGlyLeuGly

GTGGAAGCACTGGAACATCTGAGTCCAGGGGAGCAGCTTCGGGGCGACTGCATGTACGCG 1920
ValGluAlaLeuGluHisLeuSerProGlyGluGlnLeuArgGlyAspCysMetTyrAla

TCGCTCCTGGGAGGTCCACCCGCCGTGCGTCCCACTCCTTGTGCGCCTCTGGCCGAATGC 1980
SerLeuLeuGlyGlyProProAlaValArgProThrProCysAlaProLeuAlaGluCys

AAAGGTCTTTCCCTGGACGAAGGCCCGGGCAAAGGCACTGAAGAGACTGCTGAGTATTCC 2040
LysGlyLeuSerLeuAspGluGlyProGlyLysGlyThrGluGluThrAlaGluTyrSer

TCTTTCAAGGGAGGTTACGCCAAAGGGTTGGAAGGTGAGAGTCTGGGCTGCTCTGGCAGC 2100
SerPheLysGlyGlyTyrAlaLysGlyLeuGluGlyGluSerLeuGlyCysSerGlySer

AGTGAAGCAGGTAGCTCTGGGACACTTGAGATCCCGTCCTCACTGTCTCTGTATAAGTCT 2160
SerGluAlaGlySerSerGlyThrLeuGluIleProSerSerLeuSerLeuTyrLysSer

GGAGCAGTAGACGAGGCAGCAGCATACCAGAATCGCGACTACTACAACTTTCCGCTCGCT 2220
GlyAlaValAspGluAlaAlaAlaTyrGlnAsnArgAspTyrTyrAsnPheProLeuAla

CTGTCCGGGCCGCCGCACCCCCCGCCCCCTACCCATCCACACGCCCGCATCAAGCTGGAG 2280
LeuSerGlyProProHisProProProThrHisProHisAlaArgIleLysLeuGlu

AACCCGTCGGACTACGGCAGCGCCTGGGCTGCGGCGGCAGCGCAATGCCGCTATGGGGAC 2340
AsnProSerAspTyrGlySerAlaTrpAlaAlaAlaAlaAlaGlnCysArgTyrGlyAsp

TTGGCTAGCCTACATGGAGGGAGTGTAGCCGGACCCAGCACTGGATCGCCCCAGCCACC 2400
LeuAlaSerLeuHisGlyGlySerValAlaGlyProSerThrGlySerProProAlaThr

GCCTCTTCTTCCTGGCATACTCTCTTCACAGCTGAAGAAGGCCAATTATATGGGCCAGGA 2460
AlaSerSerSerTrpHisThrLeuPheThrAlaGluGluGlyGlnLeuTyrGlyProGly

GGCGGGGGCGGCAGCAGTAGCCCAAGCGATGCTGGGCCTGTAGCCCCCTATGGCTACACT 2520
GlyGlyGlyGlySerSerSerProSerAspAlaGlyProValAlaProTyrGlyTyrThr

CGGCCCCCTCAGGGGCTGGCAAGCCAGGAGGGTGACTTCTCTGCCTCTGAAGTGTGGTAT 2580
ArgProProGlnGlyLeuAlaSerGlnGluGlyAspPheSerAlaSerGluValTrpTyr

CCTGGTGGAGTTGTGAACAGAGTCCCCTATCCCAGTCCCAGTTGTGTTAAAAGTGAAATG 2640
ProGlyGlyValValAsnArgValProTyrProSerProSerCysValLysSerGluMet

GGACCTTGGATGGAGAACTACTCCGGACCTTATGGGGACATGCGTTTGGACAGTACCAGG 2700
GlyProTrpMetGluAsnTyrSerGlyProTyrGlyAspMetArgLeuAspSerThrArg
```

FIGURE 6C

```
GACCACGTTTTACCCATCGACTATTACTTCCCACCCCAGAAGACCTGCCTGATCTGTGGA 2760
AspHisValLeuProIleAspTyrTyrPheProProGlnLysThrCysLeuIleCysGly

GATGAAGCTTCTGGTTGTCACTACGGAGCTCTCACTTGTGGCAGCTGCAAGGTCTTCTTC 2820
AspGluAlaSerGlyCysHisTyrGlyAlaLeuThrCysGlySerCysLysValPhePhe

AAAAGAGCTGCGGAAGGGAAACAGAAGTATCTATGTGCCAGCAGAAATGATTGCACCATT 2880
LysArgAlaAlaGluGlyLysGlnLysTyrLeuCysAlaSerArgAsnAspCysThrIle

GATAAATTTCGGAGGAAAAATTGTCCATCGTGTCGTCTCCGGAAATGTTATGAAGCAGGG 2940
AspLysPheArgArgLysAsnCysProSerCysArgLeuArgLysCysTyrGluAlaGly

ATGACTCTGGGAGCTCGTAAGCTGAAGAAACTTGGAAATCTCAAACTACAGGAAGAAGGA 3000
MetThrLeuGlyAlaArgLysLeuLysLysLeuGlyAsnLeuLysLeuGlnGluGluGly

GAAAACTCCAGTGCTGGTAGCCCCACTGAGGACCCATCCCAGAAGATGACTGTATCACAC 3060
GluAsnSerSerAlaGlySerProThrGluAspProSerGlnLysMetThrValSerHis

ATTGAAGGCTATGAATGTCAACCTATCTTTCTTAATGTCCTGGAAGCCATTGAGCCAGGA 3120
IleGluGlyTyrGluCysGlnProIlePheLeuAsnValLeuGluAlaIleGluProGly

GTGGTGTGTGCCGGACATGACAACAACCAGCCTGATTCCTTTGCTGCCTTGTTATCTAGT 3180
ValValCysAlaGlyHisAspAsnAsnGlnProAspSerPheAlaAlaLeuLeuSerSer

CTCAACGAGCTTGGCGAGAGACAGCTTGTACATGTGGTCAAGTGGGCCAAGGCCTTGCCT 3240
LeuAsnGluLeuGlyGluArgGlnLeuValHisValValLysTrpAlaLysAlaLeuPro

GGCTTCCGCAACTTGCATGTGGATGACCAGATGGCAGTCATTCAGTATTCCTGGATGGGA 3300
GlyPheArgAsnLeuHisValAspAspGlnMetAlaValIleGlnTyrSerTrpMetGly

CTGATGGTATTTGCCATGGGTTGGCGGTCCTTCACTAATGTCAACTCTAGGATGCTCTAC 3360
LeuMetValPheAlaMetGlyTrpArgSerPheThrAsnValAsnSerArgMetLeuTyr

TTTGCACCTGACCTGGTTTTCAATGAGTATCGCATGCACAAGTCTCGAATGTACAGCCAG 3420
PheAlaProAspLeuValPheAsnGluTyrArgMetHisLysSerArgMetTyrSerGln

TGCGTGAGGATGAGGCACCTTTCTCAAGAGTTTGGATGGCTCCAGATAACCCCCCAGGAA 3480
CysValArgMetArgHisLeuSerGlnGluPheGlyTrpLeuGlnIleThrProGlnGlu

TTCCTGTGCATGAAAGCACTGCTACTCTTCAGCATTATTCCAGTGGATGGGCTGAAAAAT 3540
PheLeuCysMetLysAlaLeuLeuLeuPheSerIleIleProValAspGlyLeuLysAsn

CAAAAATTCTTTGATGAACTTCGAATGAACTACATCAAGGAACTTGATCGCATCATTGCA 3600
GlnLysPhePheAspGluLeuArgMetAsnTyrIleLysGluLeuAspArgIleIleAla
```

FIGURE 6D

```
TGCAAAAGAAAAAATCCCACATCCTGCTCAAGGCGCTTCTACCAGCTCACCAAGCTCCTG  3660
CysLysArgLysAsnProThrSerCysSerArgArgPheTyrGlnLeuThrLysLeuLeu

GATTCTGTGCAGCCTATTGCAAGAGAGCTGCATCAATTCACTTTTGACCTGCTAATCAAG  3720
AspSerValGlnProIleAlaArgGluLeuHisGlnPheThrPheAspLeuLeuIleLys

TCCCATATGGTGAGCGTGGACTTTCCTGAAATGATGGCAGAGATCATCTCTGTGCAAGTG  3780
SerHisMetValSerValAspPheProGluMetMetAlaGluIleIleSerValGlnVal

CCCAAGATCCTTTCTGGGAAAGTCAGCCCATGTATTTCCACACACAGTGAAGATTTGGAA  3840
ProLysIleLeuSerGlyLysValSerProCysIleSerThrHisSerGluAspLeuGlu

CCTAATACCCAAACCCACCTGTTCCCTTTTCAGATGTCTTCTGCCTGTTATATAACTCTG  3900
ProAsnThrGlnThrHisLeuPheProPheGlnMetSerSerAlaCysTyrIleThrLeu

CACTACTTCTCTGGCATGGGCCTTGGGGGAAATTCCTCTACTGATGTACAGTCTGTCATG  3960
HisTyrPheSerGlyMetGlyLeuGlyGlyAsnSerSerThrAspValGlnSerValMet

AACATGTTCCCCAAGTTCTATTTCCTGGGCTTTTCCTTCTTTCTTTTTCTTCTTCTCTGC  4020
AsnMetPheProLysPheTyrPheLeuGlyPheSerPhePheLeuPheLeuLeuLeuCys

CTCTTTTACCCTCCCATGGCACATTTTGAATCCGCTGCGTGTTGTGGCTCCTGCCTGTGT  4080
LeuPheTyrProProMetAlaHisPheGluSerAlaAlaCysCysGlySerCysLeuCys

TTTGAGTTTTGTTGTATTTCTTCAAGTCTGTGATGATCTTCTTGTGGCCCAGTGTCAACT  4140
PheGluPheCysCysIleSerSerSerLeuEnd

GTGCTTGTTTATAGCACTGTGCTGTGTGCCAACCAAGCAAATGTTTACTCACCTTATGCC  4200

ATGGCAAGTTTAGAGAGCTATAAGTATCTTGGGAAGAAACAAACAGAGAGAGTAAAAAAA  4260

CCAAAAAAAAAAAAAAAAAACCGAATTC                                 4288
```

FIGURE 6E

ANDROGEN RECEPTOR PROTEINS, RECOMBINANT DNA MOLECULES CODING FOR SUCH, AND USE OF SUCH COMPOSITIONS

This invention was made in the course of research supported in part by grants from the National Institutes of Health (NIH HD 16910, HD 04466, and HD 18968).

TECHNICAL FIELD OF THE INVENTION

This invention relates to recombinant DNA molecules and their expression products. More specifically this invention relates to recombinant DNA molecules coding for androgen receptor protein, androgen receptor protein, and use of the DNA molecules and protein in investigatory, diagnostic and therapeutic applications.

BACKGROUND OF THE INVENTION

The naturally occurring androgenic hormones, testosterone and its 5α-reduced metabolite, dihydrotestosterone, are synthesized by the Leydig cells of the testes and circulate throughout the body where they diffuse into cells and bind to the androgen receptor protein ("AR"). Androgens, acting through their receptor, stimulate development of the male genitalia and accessory sex glands in the fetus, virilization and growth in the pubertal male, and maintenance of male virility and reproductive function in the adult. The androgen receptor, together with other steroid hormone receptors constitute a family of trans-acting transcriptional regulatory proteins that control gene transcription through interactions with specific gene sequences.

When prostate cancer is found to be confined to the prostate gland, the treatment of choice is surgical removal. However, 50 to 80% of prostate cancer patients already have metastases at the time of diagnosis. Most of their tumors (70 to 80%) respond to the removal of androgen by castration or by suppression of luteinizing hormone secretion by the pituitary gland using a gonadotropin releasing hormone analogue alone or in combination with an anti-androgen. The degree and duration of response to this treatment is highly variable (10% live<6 months, 50% live<3 years, and 10% live>10 years.) Initially cancer cells regress without androgen stimulation, but ultimately the growth of androgen independent tumor cells continues (35). At present it is not possible to predict on an individual basis which patient will respond to hormonal therapy and for how long. If poorly responsive patients could be identified early, they could be treated by alternative forms of therapy (e.g. chemotherapy) at an earlier stage when they might be more likely to respond.

Studies on androgen receptors in prostate cancer have suggested that a positive correlation may exist between the presence of androgen receptors in cancer cells and their dependence on androgenic hormone stimulation for growth. (An analogous situation exists in mammary carcinoma where there is a correlation between estrogen receptors and regression of the tumor in response to estrogen withdrawal). However, methodological problems in the measurement of androgen receptors have prevented the routine use of androgen receptor assays in the diagnostic evaluation of prostate cancer. Prior to our preparation of androgen receptor antibodies, all androgen receptor assays were based on the binding of [$^3$H]-labeled androgen. These assays have been unreliable in human prostate cancer tissue because of the extreme lability of the androgen binding site and the presence of unlabeled androgen in the tissue. Endogenous androgen occupies the binding site on the receptor and dissociates very slowly (t ½24–48 hr at 0° C.). A further problem is that biopsy samples are quite small, making it difficult to obtain sufficient tissue for [$^3$H]-androgen binding assays. Moreover, prostate cancer is heterogenous with respect to cell types. Thus within a single biopsy sample there is likely to be an uneven distribution of cells containing androgen receptors.

Development of the male phenotype and maturation of male reproductive function are dependent on the interaction of androgenic hormones with the androgen receptor protein and the subsequent function of the receptor as a trans-acting inducer of gene expression. It has become well established over the past twenty-five years that genetic defects of the androgen receptor result in a broad spectrum of developmental and functional abnormalities ranging from genetic males (46,XY) with female phenotype to phenotypically normal males with infertility. Isolation of the structural gene for the androgen receptor makes it possible to define the nature of these genomic defects in molecular terms. Analysis of the functional correlates of the genetic detects may lead to a better understanding of the regulation of androgen receptor gene expression and of the mechanism of androgen action in male sexual development and function.

The androgen insensitivity syndrome, known also as testicular feminization, is characterized by an inability to respond to androgen due to a defect in the androgen receptor, the protein that mediates the action of androgen within the cell. Androgen insensitivity is an inherited X-linked trait that occurs in both complete and incomplete forms. The complete form results in failure of male sex differentiation during embryogenesis and absence of virilization at puberty. The result is a 46,XY genetic male with testes and male internal ducts. The testes produce normal amounts of testosterone and Mullerian inhibiting substance. Consequently development of the uterus is inhibited as in the normal male. Because of the inability to respond to androgen, the external genitalia remain in the female phenotype with normal clitoris and labia. A small vagina develops from the urogenital sinus and ends in a blind pouch. At puberty feminization with breast development and female contours occur in response to testicular estrogen, however, there is no growth of sexual hair even though circulating testosterone concentrations are equal to or greater than levels in the normal male.

Incomplete forms of the androgen insensitivity syndrome include a spectrum of phenotypes resulting from varying degrees of incomplete androgen responsiveness. At one extreme, individuals have mild enlargement of the clitoris and sparse pubic hair. The opposite extreme is characterized by more complete masculinization with varying degrees of hypospadias deformity but predominantly a male phenotype. It has been reported that some adult men with severe oligospermia or azoospermia who are otherwise normal, have defects in the androgen receptor. These may include as many as 10% of infertile males.

The genetic defect eliciting this range of abnormalities is thought to be a single biochemical event at the level of the gene for the androgen receptor. The androgen receptor is a high affinity androgen binding protein that mediates the effects of testosterone and dihydrotestosterone by functioning as a trans-acting inducer of gene expression. For proper male sexual development to occur, there is a requirement for androgen and its receptor at a critical time during embryogenesis and during puberty. The majority of individuals with the androgen insensitivity syndrome have a history of affected family members, although about a third are thought to represent new mutations of this X-linked disorder. The incidence ranges from 1 in 20,000 to 60,000 male births.

In studies of families with clinical evidence of the androgen insensitivity syndrome, four main categories were recognized that range from the most severe, complete absence of receptor binding activity in a genetic male with female phenotype, to qualitatively normal receptor in affected individuals. Second in severity are affected individuals with qualitatively abnormal androgen binding by receptor present in normal levels. Examples include the failure of sodium molybdate (a reagent often used in studies on steroid receptors) to stabilize the receptor of affected individuals when molybdate is known to stabilize the wild-type receptor. Lability of the receptor under conditions that normally cause transformation has also been reported. A third group expresses a decreased amount of receptor with wild-type in vitro binding characteristics. The final grouping contains those androgen insensitivity patients in whom no abnormality in receptor is detected. In a recent study of this form of the syndrome, the androgen receptor was as capable of binding oligonucleotides as the wild-type receptor. Indeed, with the techniques available until only recently, it has been difficult in certain cases to document an androgen receptor defect in affected individuals.

Experimental methods used in assessing receptor detects in the past have relied on the ability of receptor to bind androgen with high affinity. The limitation of this methodology is that it is not possible to distinguish between the lack of expression of the receptor and loss of androgen binding activity. An example of how inadequate methodology complicates diagnosis is the absence of detectable receptor binding activity in patients who are partially virilized. It is theoretically possible for a mutation to occur which allows the receptor with defective androgen binding activity to induce gene transcription. Biologically active truncated forms of the glucocorticoid receptor that lack steroid binding activity but retain the DNA binding domain have been demonstrated using genetically engineered mutants.

Purification of the androgen receptor has been difficult to accomplish due to its low concentration and high degree of instability. Reported attempts at purification using either conventional methods of column chromatography or steroid-affinity chromatography have yielded insufficient amounts of receptor protein to allow even the preparation of monoclonal antibodies.

An early report on the partial purification of the androgen receptor was disclosed by Mainwaring et al. in "The use of DNA-cellulose chromatography and isoelectric focusing for the characterization and partial purification of steroid-receptor complexes," *Biochem J*, 134, 113–127 (1973). They used DNA-cellulose chromatography and isoelectric focusing to isolate the receptor from rat ventral prostate and determined its physiochemical properties. This group was among the first to attempt the use of steroid affinity chromatography in conjunction with conventional chromatography, using the affinity label 17B-bromoacetoxytestosterone in receptor purification (See Mainwaring et al., "Use of the affinity label 17B-bromoacetoxytestosterone in the purification of androgen receptor proteins," Perspectives in Steroid Receptor Research, (1980)). Partial purification of androgen receptor has also been attempted from other tissue sources, such as ram seminal vesicles (See Foekens et al., Molecular Cellular Endocr, 23, 173–186 (1981) and Foekens et al., "Purification of the androgen receptor of sheep seminal vesicles," Biochem Biophys Res Comm, 104, 1279–1286 (1982)). The partially purified receptor displayed characteristics of a proteolyzed receptor, but a purification of 2,000 fold was reported with a recovery of 33% (See Foekens et al., "Purification of the androgen receptor of sheep seminal vesicles," Biochem Biophys Res Comm, 104, 1279–1286 (1982)). Later attempts at purification continued to combine steroid affinity chromatography with conventional techniques, reportedly achieving significant purification, but recoveries too low for further analysis (See Chang et al., "Purification and characterization of androgen receptor from steer semenal vesicle," Biochemistry 21, 4102–4109 (1982), Chang et al., "Purification and characterization of the androgen receptor from rat ventral prostate," Biochemistry 22, 6170–6175 (1983) and Chang et al., "Affinity labeling of the androgen receptor in rat prostate cytosol with 17B-[(bromoacetyl)oxy]-5-alpha-androstan-3-one," Biochemistry 23, 2527–2533 (1984)). More recent studies examine the effectiveness of a variety of immobilized androgens for their ability to bind the androgen receptor (See De Larminat et al., "Synthesis and evaluation of immobilized androgens for affinity chromatography in the purification of nuclear androgen receptor," The Prostate 5, 123–140 (1984) and Bruchovsky et al, "Chemical demonstration of nuclear androgen receptor following affinity chromatography with immobilized ligands," The Prostate 10, 207–222 (1987)). Despite these efforts, the receptor has not been purified to homogeneity and the quantities of purified androgen receptor obtained have been insufficient for the production of antisera.

Clinical assays for the androgen receptor now include several methods. The most common is the binding of tritium-labeled hormone and measurement of binding using a charcoal adsorption assay. Either a natural androgen, such as dihydrotestosterone, or synthetic androgen, such as mibolerone or methyltrienolone (R1881), can be used. An advantage of the latter in human tissue is that it is not significantly metabolized and does not bind to the serum androgen binding protein, sex steroid binding globulin. A limitation of radioisotope labeling of receptor is interference caused by endogenous androgen. Although exchange assays for the androgen receptor have been described (See Carroll et al., J Steroid Biochem 21, 353–359 (1984) and Traish et al., J Steroid Biochem 23, 405–413 (1985)), their effectiveness is limited by the slow kinetics of dissociation of the endogenous receptor-bound androgen.

Another method used to assess receptor status is autoradiography. In this method disclosed in Barrack et al., "Current concepts and approaches to the study of prostate cancer," Progress in Clinical and Biological Research, 239, 155–187 (1987) the radioactively labeled androgen is incubated with slide-mounted tissue sections of small tissue biopsy specimens which are then frozen, sectioned and fixed. Nuclear localization of radioactivity is detected by exposure of tissue sections to x-ray film. This technique requires considerable technical expertise, is labor intensive, and requires extended periods of exposure time. It is therefore of limited usefulness in general clinical assays. Another problem is high levels of background signal, i.e. a high noise/signal ratio, making it difficult to distinguish receptor-bound nuclear radioactivity from unbound radioactivity distributed throughout the cells.

WO 87/05049 (Shine) discloses a method for the production of purified steroid receptor proteins, specifically estrogen receptor proteins, through the expression of recombinant DNA encoding for such proteins in eukaryotic host cells. However, the reference does not disclose the sequence for androgen receptor protein, nor does it disclose a method for obtaining such a sequence.

SUMMARY OF THE INVENTION

The present invention provides a DNA sequence characterized by a structural gene coding for a polypeptide having substantially the same biological activity as androgen receptor protein. A DNA sequence encoding androgen receptor protein or a protein having substantially the same biological activity as androgen receptor activity is also provided. DNA sequences may be obtained from cDNA or genomic DNA, or prepared using DNA synthesis techniques.

The invention further discloses cloning vehicles comprising a DNA sequence comprising a structural gene encoding a polypeptide having substantially the same biological activity as androgen receptor protein. Cloning vehicles comprising a DNA sequence encoding androgen receptor protein or a protein having substantially the same biological activity as androgen receptor protein are also provided. The cloning vehicles further comprise a promoter sequence upstream of and operatively linked to the DNA sequence. In general the cloning vehicles will also contain a selectable marker, and, depending on the host cell used, may contain such elements as regulatory sequences, polyadenylation signals, enhancers and RNA splice sites.

The invention further provides cells transfected or transformed to produce androgen receptor protein or a protein having substantially the same biological activity as androgen receptor protein.

A further aspect of the invention provides a purified androgen receptor protein and purified polypeptides and proteins having substantially the same biological activity as androgen receptor protein, and methods for producing such proteins and polypeptides.

BRIEF DESCRIPTION OF THE DRAWINGS

FIGS. 1A–1C show a comparison of DNA-binding domains of the human androgen receptor (hAR) with members of the nuclear receptor family. (FIG. 1A) is a comparison of oligo A nucleotide sequence with sequences of hAR and other nuclear receptors: hPR, human progesterone receptor; hMk, human mineralocorticoid receptor; hGR, human glucocorticoid receptor; hER, human estrogen receptor; hT3R, human thyroid hormone receptor; hRAR, human retinoic acid receptor. Chromosomal locations are shown in parentheses at the left. Nucleotide identity between oliyo A and hAR is indicated with an asterisk. The percent homology with oligo A is in parentheses at the right of each sequence. (FIG. 1B) shows the the structure of fibroblast clone ARHFL1 human fibroblast clone [1]). Nucleotide residues are numbered from the 5'-terminus. Restriction endonuclease sites were determined by mapping or were deduced from DNA sequence. The TGA translation termination codon, determined by comparison with hPR, hMR and hGR, follows a long open reading trame containing sequences homologous to those of other steroid receptors. Arrows indicate exon boundaries in genomic clone X05Ak. The hatched area is the putative DNA binding domain. (FIG. 1C) shows a comparison of amino acid sequences of the AR DNA-binding domain with sequences of the nuclear receptor family. AR amino acid sequence was deduced from nucleotide sequence of clone ARHFL1 and is numbered beginning with the first conserved cysteine residue (+). Amino acid numbers in parentheses at the left indicate the residue number of the first conserved cysteine from the references indicated above. Percent homology with hAR is indicated in parentheses on the right. The region of the DNA-binding domain from which the oligo A sequence was derived is underlined in hAR. Coding DNA of residues 1 to 31 is contained within genomic clone X05AR. Abbreviations in addition to those described above are cVDR, chicken vitamin D receptor, and vERBA, erb A protein from avian erythroblastosis virus. Abbreviations for amino acid residues are:
A, Ala; C, Cys; D, Asp; E, Glu; F, Phe; G, Gly; H, His; I, Ile; K, Lys; L, Leu; M, Met; N, Asn; P, Pro; Q, Gln; R, Ary; S, Ser; T, Thr; V, Val; W, Trp; and Y, Tyr.

(FIG. 2A) shows the structure of pCMVAR in the expression vector pCMV containing tne human cytomeyalovirus(CMV) promoter of the immediate early gene, poly(A) addition-transcription terminator region of the human growth hormone gene (hGH poly A),SV40 origin of replication (SV40 Ori), and a polylinker region for insertion of cDNAs. The plasmid pTEBR contains the ampicillin resistance gene (Amp). (FIG. 2B) shows saturation analysis of [$^3$H]dihydrotestosterone binding in extracts of pCMVAR transtection of COS M6 cells. Portions of cytosol (0.1 ml, 0.3 mg/ml protein) were incubated overnight at 4° C. with increasing concentrations of $^3$H-labeled hormone and analyzed by charcoal adsorption. Nonspecific binding increased from 18% to 37% of total bound radioactivity. (FIG. 2C) shows a Scatchard plot analysis of [$^3$H]dihydrotestosterone binding. Error estimation was based on linear regression analysis (r=0.966). (FIG. 2D) illustrates the competition of unlabeled steroids for binding of 5 nM [$^3$H]dihydrotestosterone in transtected COS M6 cell extracts. Unlabeled steroids were added at 10- and 100-fold excess of labeled hormone. Specific binding was determined as previously described.

FIGS. 4A–4H show the double-stranded DNA sequence encoding the human androgen receptor protein.

FIGS. 5A–5F show the complete single strand sequence (5085 bases) of the human androgen receptor and the deduced amino acid sequence. No intron sequence is included.

FIGS. 6A–6E show the complete single strand sequence (4260 bases) of the rat androgen receptor and the deduced amino acid sequence.

DETAILED DESCRIPTION OF THE INVENTION

Figures 1A, 1B:
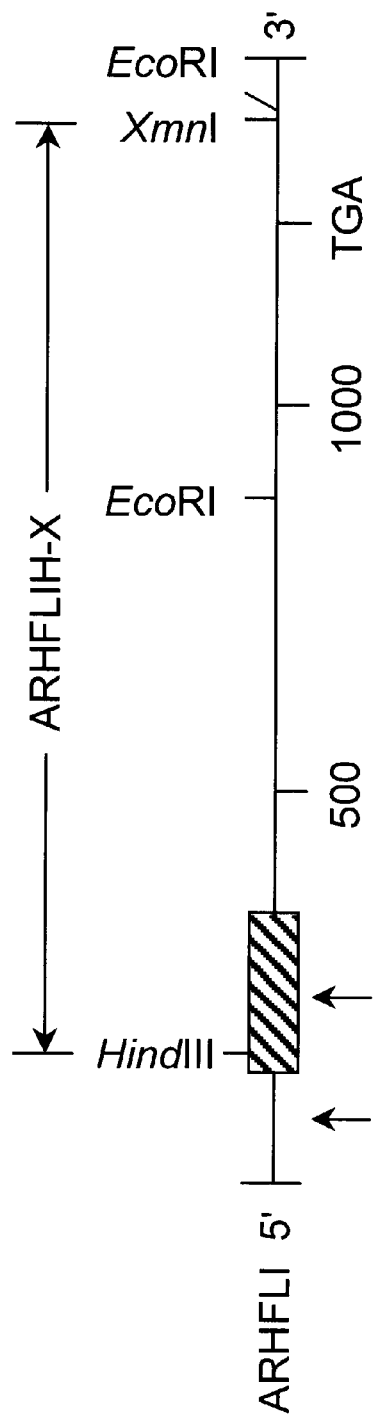

In the description the following terms are employed:
Nucleotide

A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U"). A and G are purines, abbreviated to R, and C, T, and U are pyrimidines, abbreviated to Y.

DNA Sequence
  A linear series of nucleotides connected one to the other by phosphodiester bonds between the 3' and 5' carbons of adjacent pentoses.
Codon
  A DNA sequence of three nucleotides (a triplet) which encodes through mRNA an amino acid, a translational start signal or a translational termination signal. For example, the nucleotide triplets TTA, TTG, CTT, CTC, CTA and CTG encode for the amino acid leucine ("Leu"), TAG, TAA and TGA are translational stop signals and ATG is a translational start signal.
Reading Frame
  The grouping of codons during translation of mRNA into amino acid sequences. During translation the proper reading frame must be maintained. For example, the sequence GCTGGTTGTAAG may be translated in three reading frames or phases, each of which affords a different amino acid sequence:
    GCT GGT TGT AAG—Ala-Gly-Cys-Lys
    G CTG GTT GTA AG—Leu-Val-Val
    GC TGG TTG TAA A—Trp-Leu-(STOP)
Polypeptide
  A linear series of amino acids connected one to the other by peptide bonds between the α-amino and carboxy groups of adjacent amino acids.
Genome
  The entire DNA of a substance. It includes inter alia the structural genes encoding for the polypeptides of the substance, as well as operator, promoter and ribosome binding and interaction sequences including sequences such as the Shine-Dalgarno sequences.
Structural Gene
  A DNA sequence which encodes through its template or messenger RNA ("mRNA") a sequence of amino acids characteristic of a specific polypeptide.
Transcription
  The process of producing MRNA from a structural gene.
Translation
  The process of producing a polypeptide from mRNA.
Expression
  The process undergone by a structural gene to produce a polypeptide. It is a combination of transcription and translation.
Plasmid
  A non-chromosomal double-stranded DNA sequence comprising an intact "replicon" such that the plasmid is replicated in a host cell. When the plasmid is placed within a unicellular organism, the characteristics of that organism are changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".
Phage or Bacteriophage
  Bacterial virus many of which include DNA sequences encapsidated in a protein envelope or coat ("capsia"). In a unicellular organism a phage may be introduced as free DNA by a process called transfection.
Cloning Vehicle
  A plasmid, phage DNA or other DNA sequences which are able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.
Cloning
  The selection and propagation of a single species.
Recombinant DNA Molecule
  A hybrid DNA sequence comprising at least two nucleotide sequences, the first sequence not normally being found together in nature with the second.
Expression Control Sequence
  A DNA sequence of nucleotides that controls and regulates expression of structural genes when operatively linked to those genes.

To attain the objects of this invention it was necessary to determine the amino acid sequence and the DNA sequence of the structural gene encoding androgen receptor protein. One conventional approach would involve starting with the purified androgen receptor protein. However, as described above, significant amounts of the protein for such purposes have not been obtained.

An alternative approach to circumvent the overwhelming difficulty of androgen receptor protein purification is direct isolation of the DNA encoding the messenger RNA for androgen receptor protein.

Our strategy for isolating AR DNA was based on evidence that the AR gene is X-linked and that no other steroid receptor gene is located on the X chromosome. Sequence data are available from cDNAs for glucocorticoid, estrogen, progesterone, mineralocorticoid and vitamin D receptors. Comparison of the derived amino acid sequences has revealed a central region of high cysteine content which was found also in the v-erb A oncogene product recently identitied as the thyroid hormone receptor. Within this 61–63 amino acid region is an arrangement of 9 cysteine residues that are absolutely conserved among steroid receptors thus far characterized. The overall homology among sequences in this conserved region ranges between 40 and 90%. We assumed that AR would resemble other members of the steroid receptor family in the conserved DNA-binding domain.

A human X chromosomal library was screened with the synthetic oligo nucleotide probe A (Oligo A sequence=$^{5'}$CTT TTG AAG AAG ACC TTA CAG CCC TCA CAG GT$^{3'}$) of FIG. 1 (A) designed as a consensus sequence from the conserved sequence of the DNA-binding domain of other steroid receptors. Screening the library with the oligo A probe resulted in several recombinants whose inserts were cloned into bacteriophage M13 DNA and sequenced. One recombinant clone (Charon 35 X05AR) (human genomic clone [1]) contained a sequence similar to, yet distinct from, the DNA-binding domains of other steroid receptors. It had 84% sequence identity with oligo A, while other receptor DNAs were 78% to 91% homologous with the consensus oligonucleotide.

From the nucleotide sequence just 5' of the DNA binding domain, oligonucleotide probe B (Oligo B sequence=$^5$GGA CCA TGT TTT UCC CAT TGA CTA TTA CTT TCC ACC CC$^3$) was synthesized and used to screen bacteriophage lambda gtll cDNA libraries from human epididymis and cultured human foreskin fibroblasts. Recombinant phage (unamplified) screened with this oligonucleotide by in situ hybridization revealed one positive clone in each library. The epidydimal clone (gtll ARHEL1)(human epididymis clone [1]) contained the complete DNA-binding domain and approximately 1.5 kb of upstream sequence, whereas the fibroblast clone (gtll ARHFL1)(human fibroblast clone [1]) shown in FIG. 1(B) contained the DNA-binding domain and 1.5 kb of downstream sequence. The DNA-binding domains of the cDNA isolates were identical to that of the genomic exon sequence.

Figure 2B:
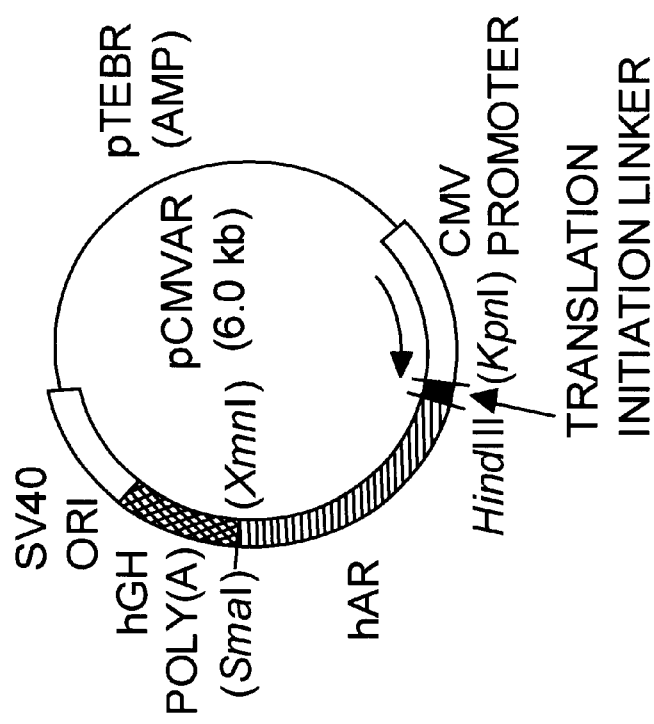
FIGS. 2A–2D illustrate the steroid binding properties of expressed AR cDNA.
Figure 2A:
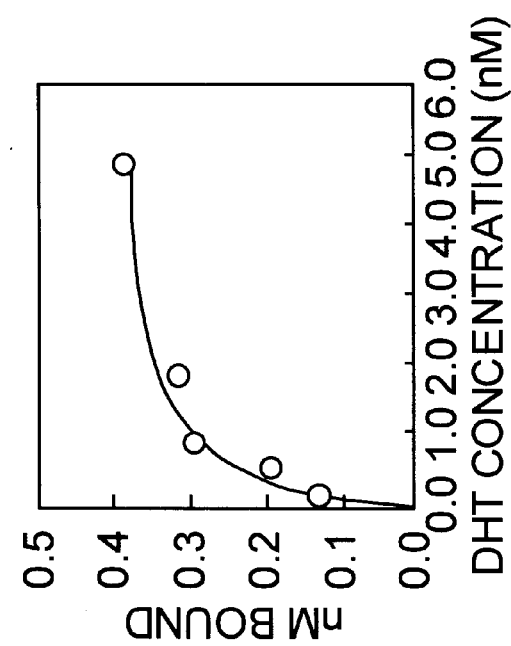
Figure 2D:
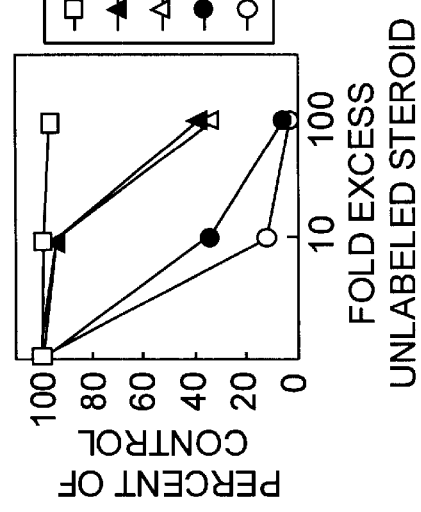
Figure 2C:
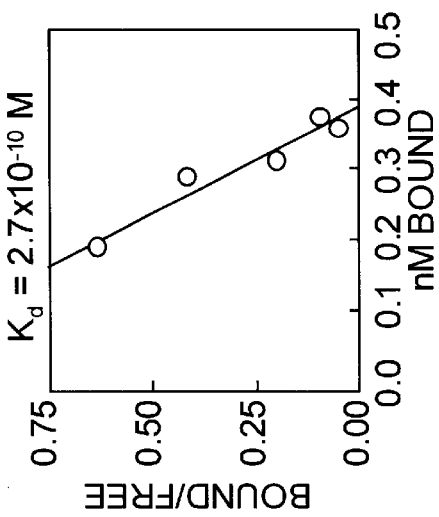

Transient expression in monkey kidney cells (COS M6) demonstrated that the human foreskin fibroblast cDNA fragment encodes the steroid-binding domain of hAR. A DNA fragment (ARHFLIH-X) extending 5' to 3' from the Hind III site within the putative DNA-bindiny domain through the stop codon (TGA) was cloned into pCMV as shown in FIG. 2(A). Expression was facilitated by adding to the 5' end a consensus translation initiation sequence containing the methionine codon (ATG) in reading frame. Transfection of the recombinant construct produced a protein with high-affinity for [$^3$H]dihydrotestosterone, FIG. 2(C) saturable at physiological levels of hormone. See FIG. 2(B). The binding constant [$K_d$=2.7 (+1.4)×10$^{-10}$M) was nearly identical to that of native AR. The level of expressed protein, 1.3 pmol per milligram of protein, was 20 to 60 times greater than that in male reproductive tissues. Mock transfections without plasmid or transfections with plasmid DNA lacking th AR insert yielded no specific binding of dihydrotestosterone. FIG. 2(D) shows steroid specificity was identical to that of native AR, with highest affinity for dihydrotestosterone and testosterone, intermediate affinity for progesterone and estradiol, and low affinity for cortisol.

Figure 3:
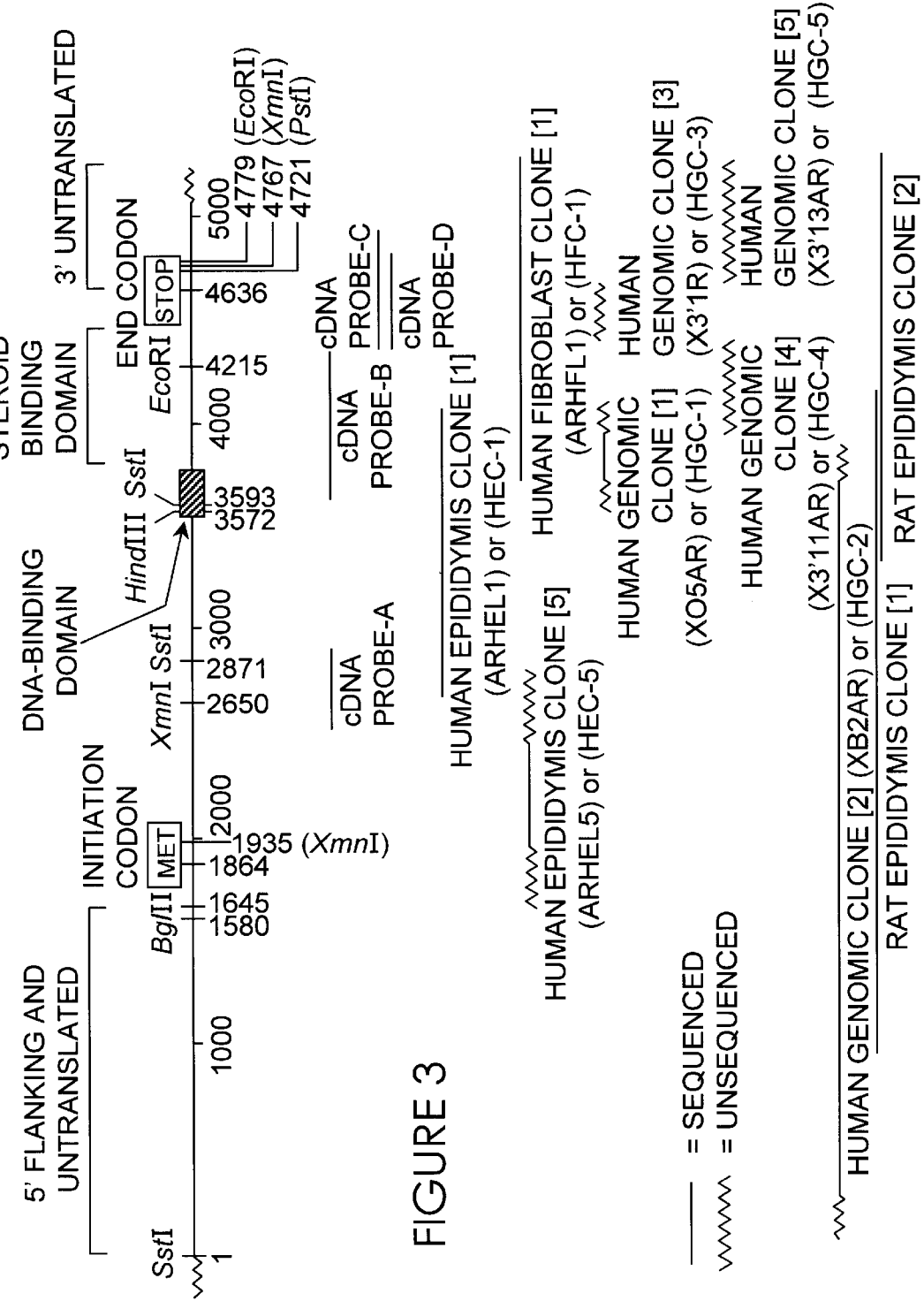
FIG. 3 is a compiled clone map of the human androgen receptor. The map shows the structure of the human androgen receptor gene and the relative positions of the nucleic acid sequences contained in the cDNA probes [A], [B], [C] and [D], human fibroblast clone [1], human epididymis clones [1] and [5], human genomic clones [1], [2], [3], [4] and [5], and rat epididymis clones [1] and [2].

FIG. 3 is a clone map compiled to show the human androgen receptor gene and the nucleic acid sequences in the cDNA clones, human genomic clones, human fibroblast clones, human epididynmis clones, and rat epididymis clones. Human fibroblast clone [1] extended through the stop codon or the C-terminal end of the androgen receptor protein. To isolate and elucidate the sequence of the 5' or N-terminal end of the androgen receptor protein, we used a EcoRl/Sstl fragment (EcoRl site was from the linker) from the 5' end of human epididymis clone [1] as a probe (cDNA probe [A]), to rescreen the human X chromosonial library by standard techniques. By these techniques, human genomic clone [2] was isolated and in turn used as a probe to rescreen a human epididynis library and isolate human epididymis clone [5]. The N-terminal sequence was elucidated along with the 5' flanking sequence of the androgen receptor protein and gene. Human genomic clones [3], [4] and [5] for the sequence 3' of human genomic clone [1] were obtained using cDNA probes B [a Hind III/EcoRl fragment] and C [an EcoRl fragment], by screening and isolating by standard techniques.

Two rat clones, rat epididymis clones [1] and [2], were isolated from a rat epididymis cDNA library using as probes the complete human epididymis clone [1] and a EcoRl/Pstl fragment, cDNA probe [D], respectively. These rat clones contained the entire protein coding sequence for the rat androgen receptor, plus flanking 5' and 3' untranslated sequences which were used to confirm the sequence of the human androgen receptor.

The complete double-stranded sequence encoding the human androgen receptor protein was determined and is set forth in FIG. 4. The single-stranded DNA sequence encoding human androgen receptor protein along with the amino acid sequence which it codes for are set forth in FIG. 5. The single stranded DNA sequence and the amino acid sequence for the rat androgen receptor protein is set forth in FIG. 6

Recombinant DNA clones human fibroblast clone [1] isolated from human foreskin fibroblast cDNA gtll expression library, human epididymis clones [1] and [5] isolated from human epididymis cDNA gtll expression library were deposited in the American Type Culture Collection with accession numbers ATCC #40439, ATCC #40442 and ATCC #40440 respectively. Human genomic clones [1], [2], [3], [4] and [5] which were isolated from human X chromosome lambda Charon 35 library available as ATCC #57750 have been deposited with the American Type Culture Collection with accession numbers ATCC #40441, ATCC #40443, ATCC #40444, ATCC #40445 and ATCC #40446 respectively.

A wide variety of host-cloning vehicle combinations may be usefully employed in cloning the double stranded DNA disclosed herein. For example, useful cloning vehicles may include chroomosomal, non-chromosomal and synthetic DNA sequences such as various known bacterial plasmids and wider host range plasmids such as pCMV and vectors derived from combinations of plasmids and phage DNA such as plasmids which have been modified to employ phage DNA expression control sequences. Useful hosts may include bacterial hosts, yeasts and other fungi, animal or plant hosts, such as Chinese Hamster Ovary cells (CHU, or monkey kidney cells (COS M6), and other hosts. The particular selection of host-cloning vehicle combinations may be made by those of skill in the art after due consideration of factors such as the source of the DNA- i.e. genomic or cDNA.

Cloning vehicles for use in carrying out the present invention will further comprise a promoter operably linked to the DNA sequence encoding the androgen receptor protein. In some instances it is preferred that cloning vehicles further comprise an origin of replication, as well as sequences which regulate and/or enhance expression levels, depending on the host cell selected.

Techniques for transforming hosts and expressing foreign DNA cloned in them are well known in the art (See, for example, Maniatis et al., infra). Cloning vehicles used for expressing foreign genes in bacterial hosts will generally contain a selectable marker, such as a gene for antibiotic resistance, and a promoter which functions in the host cell.

Eukaryotic microorganisms, such as the yeast Saccharomyces cerevisiae, may also be used as host cells. Cloning vehicles will generally comprise a selectable marker, such as the nutritional marker TRP, which allows selection in a host strain carrying a trpt mutation. To facilitate purification of an androgen receptor protein produced in a yeast transformant, a yeast gene encoding a secreted protein may be joined to the sequence encoding androgen receptor protein.

Higher eukaryotic cells can also serve as host cells in carrying out the present invention. Cultured mammalian cells are preferred. Cloning vehicles for use in mammalian cells will comprise a promoter capable of directing the transcription of a foreign gene introduced into a mammalian cell. Also contained in the expression vector is a polyadenylation signal, located downstream of the insertion site. The polyadenylation signal can be that of the cloned androgen receptor gene, or may be derived from a heterologous gene.

A selectable marker, such as a gene that confers a selectable phenotype, is generally introduced into the cells along with the gene of interest. Preferred selectable markers include genes that confer resistance to drugs, such as neomycin, hygromycin and methotrexate. Selectable markers may be introduced into the cell on a separate plasmid at the same time as the gene of interest, or they may be introduced on the same plasmid.

The copy marker of the integrated gene sequence can be increased through amplification by using certain selectable markers. Through selection, expression levels may be substantially increased.

Androgen receptor proteins may be purified from the host cells or cell media according to the present invention using techniques well known to those in the art. Such proteins may be utilized to produce monoclonal or polyclonal antibodies according to the techniques described below.

The techniques of this invention offer considerable advances over existing technology for measurement of androgen receptor. Utilizing proteins and peptides containing the disclosed sequences monoclonal or polyclonal antibodies can be produced for use as immunochemical reagents in immunodiagnostic assays. For example, radioimmunoassays and ELISA assays can be developed utilizing these reagents which will allow detection and quantification of androgen receptor in the presence of endogenous androgen since such androgen will not interfere with antibody binding to the receptor.

Immunocytochemistry utilizing our reagents enables determination and quantification of the cellular distribution of the androgen receptor in tumor tissues, which are often heterogenous in composition. This assay offers great potential for diagnostic evaluation of prostate cancer to determine to responsiveness to androgen withdrawal therapy.

In addition, the antibodies produced using the disclosed amino acid sequences can also be used in processes for the purification of androgen receptor protein produced by the above methods. One such purification process is disclosed in Logeat, F., et al., *Biochemistry* vol. 24 (1985), pp. 1029–1035, which is incorporated by reference herein.

Androgen receptor proteins and polypeptides synthesized from the deduced amino acid sequence can be used as immunogens for the preparation of antibodies to the androgen receptor. Peptides for such use range in length from about 3 to about 958 amino acids in length and are preferably from about 15 to about 30 amino acids in length. Shorter peptides may have significant sequence homology to other steroid receptor proteins and larger peptides may contain multiple antigenic determinants; these properties could result in antibodies with cross-reactivities to other steroid receptor proteins.

Peptides can be synthesized from amino acid sequences in the $NH_2$-terminal region, the DNA-binding domain, and the carboxyl-terminal steroid binding domain. Peptide selection will be based on hydropathic plots, selecting hydrophilic regions that are more likely exposed on tne receptor surface. For diagnostic purposes preferred sequences will be selected from the $NH_2$-terminal region where there is the least homology with other steroid receptor proteins.

Peptides for use as immunogens can be synthesized using techniques available to one of ordinary skill in the art. For example, peptides corresponding to androgen receptor sequences can be synthesized using tBOC chemistry on a Biosearch Model 9500 peptide synthesizer. Peptide purity is assessed by high pressure liquid chromatography. Peptioes can be conjugated to keyhole limpet hemocyanin through cysteine residues using the coupling agent m-maleimido-benzoyl-N-hydroxysuccinimide ester. One can also prepare resin-bound peptides utilizing the p-(oxymethyl benzamide) handle to attach the C-terminal amino acid to solid-phase resin support.

Proteins and peptides of this invention can be utilized for the production of polyclonal or monoclonal antibodies. Methods for production of such antibodies are known to those of ordinary skill in the art and may be performed without undue experimentation. One method for the production of monoclonal antibodies is described in Kohler, G., et al., "Continuous Culture of Fused Cells Secreting Antibody of Predefined Specificity," *Nature*, vol. 256 (1975), p. 495, which is incorporated herein by reference. Polyclonal antibodies, by way of example, can be produced by the method described below.

Peptide conjugates or resin-bound peptides can be injected into rabbits according to the procedure of Vaitukaitis et al., J Clin Endocrinol Metab, 33, 988–991 (1971) using a standard immunization schedule. Antisera titers can be determined in the ELISA assay.

For example, one androgen receptor sequence, $NH_2$-Asp-His-Val-Leu-Pro-Ile-Asp-Tyr-Tyr-Phe-Pro-Pro-Gln-Lys-Thr in the 5' region upstream from the DNA-binding domain, was used to raise antisera in rabbits. The antisera react selectively at a dilution of 1 to 500 with the androgen receptor both in its untransformed 8-10S form and in its 4-5S transformed form. Receptor sedimentation on sucrose gradients increases from 4 to 8-10S in the presence of antiserum at high ionic strength and from 8-10S to 11-12S at low ionic strength sucrose gradients. In the ELISA reaction against the peptide used as immunogen, reactivity was detectable at 1 to 25,000 dilution. This antiserum at a dilution of 1 to 3000 was found effective in staining nuclear androgen receptor in rat prostate and other male accessory sex glands.

Our invention provides new molecular probes comprising complementary DNA sequences derived from the deduced sequences encoding the androgen receptor for diagnostic purposes. Such probes may be used to detect the presence of androgen receptor mRNA in tumor cells. Such probes may also be used for detection of androgen receptor gene defects. Androgen receptor complementary DNA sequences can be used as hybridization probes to detect abnormalities in the androgen receptor gene or in its messenger RNA.

Androgen receptor DNA sequences disclosed and complementary RNA sequences can be used to construct probes for use in DNA hybridization assays. An example of one such hybridization assay and methods for constructing probes for such assays are disclosed in U.S. Pat. No. 4,683,195 to Mullis et al., U.S. Pat. No. 4,683,202 to Mullis, U.S. Pat. No. 4,617,261 to Sheldon, III et al., U.S. Pat. No. 4,683,194 to Salki et al., and U.S. Pat. No. 4,705,886 to Levenson et al., which are hereby incorporated by reference.

By example, one method for detecting gene deletion utilizes Southern blotting and hybridization. DNA can be isolated from cultured skin fibroblasts or from leukocytes obtained from blood. DNA is cut with restriction enzymes, electrophoresed on an agarose gel, blotted onto nitrocellulose, and hybridized with $[^{32}P]$-labeled androgen receptor DNA (see Maniatis, T. et al., Molecular Cloning, A Laboratory Manual, Cold Spring Harbor Laboratory, 1982, incorporated by reference herein).

In addition, small mutations can be detected utilizing methods known to one of ordinary skill in the art, from cultured skin fibroblasts of the affected individual. A cDNA library can been prepared using standard techniques. The androgen receptor clones can be isolated using a $[^{32}P]DNA$ AR probe. The clones AR cDNA can then be sequenced and compared to normal AR cDNA sequences.

Alternatively genomic DNA can be isolated from blood leukocytes or cultured skin fibroblasts of the affected individual. The DNA is then subjected to restriction enzyme digestion, electrophoresis and is blotted onto nitrocellulose. Synthetic oligonucleotides can be used to bracket specific exons. Exon sequences are amplified using the polymerase chain reaction, cloned into M13 and sequenced. The sequences are compared to normal human AR DNA sequences.

Another method of identifying small mutations or deletions takes advantage of the ability of RNase A to cleave regions of single stranded RNA in RNA:DNA hybrids. Genomic DNA isolated from fibroblasts of affected individuals is hybridized with radioactive RNA probes (Promego Biotec) prepared from wild-type androgen receptor cDNA. Mismatches due to mutations would be cleaved by RNase A and result in altered sized bands relative to wild-type on denaturing polyacrylamide gels.

Restriction fragment length polymorphism (RFLP) linked to the androgen receptor gene locus may be used in prenatal diagnosis and carrier detection of androgen insensitivity. For example, the presence of RFLPs in normal individuals is first established by isolating DNA from lymphocytes of at least six females (total of 12 X chromosomes). DNA can be isolated using the proteinase K procedure and fragmented using a battery of restriction enzymes. Preferred are those enzymes that contain the dinucleotide sequence CG in their recognition sequence. Southern blots are screened with 5–10 kb androgen receptor genomic fragments which if possible lack repetitive DNA. For those regions containing repetitive elements, total human genomic DNA can be added as competitor in the hybridization reaction. Alternatively, one can subclone selected regions to yield a probe free of repetitive elements.

Figure 7:
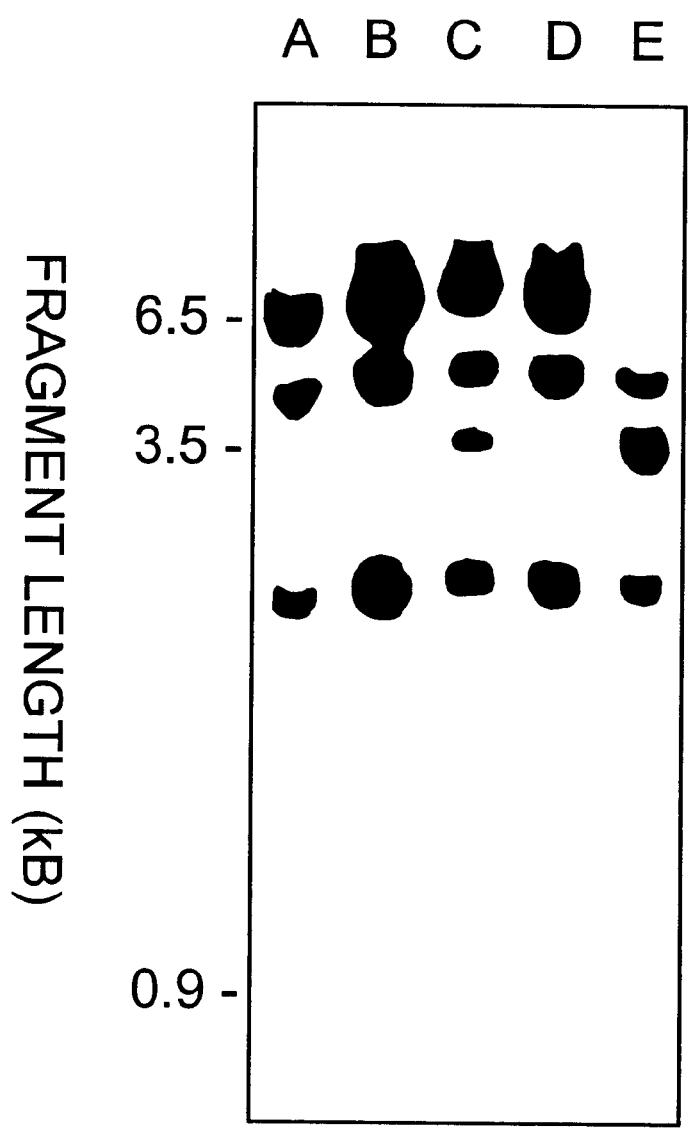
FIG. 7 is a photograph showing restriction fragment length polymorphisms in the human androgen receptor gene.
Figure 8:
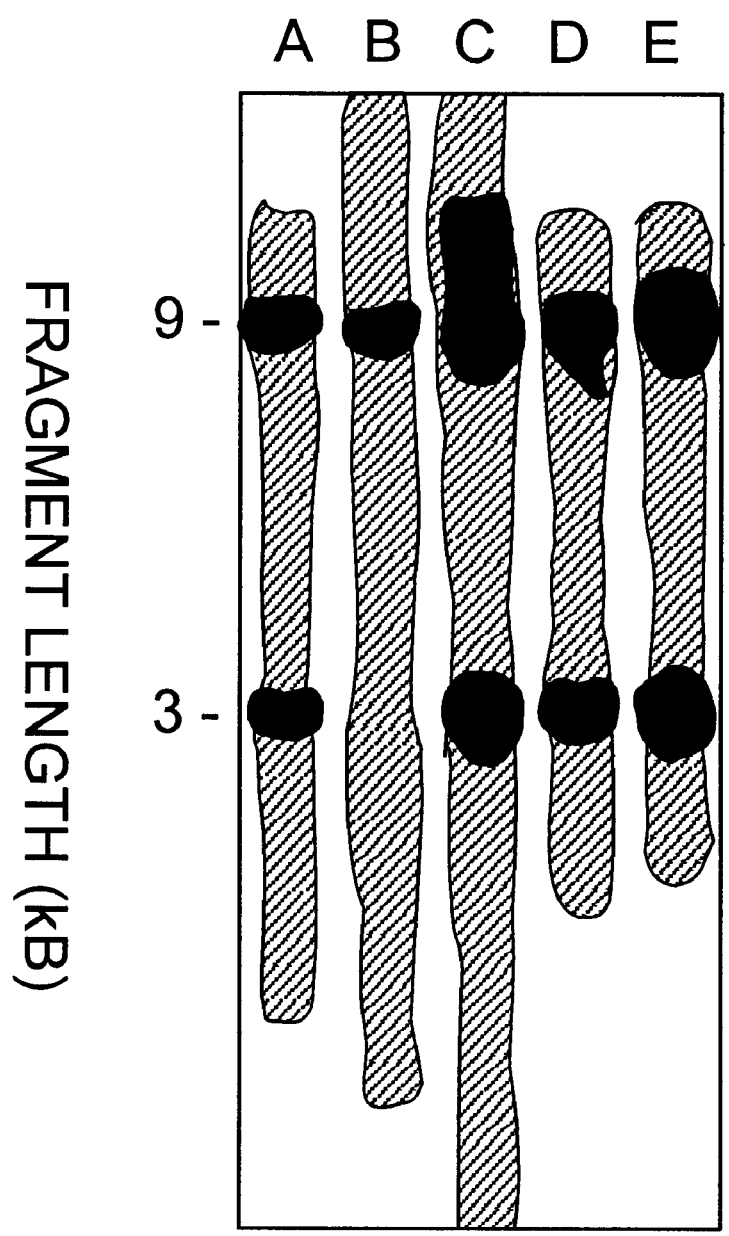
FIG. 8 is a photograph showing a Southern blot analysis in the human androgen receptor gene in complete androgen insensitivity syndrome patients.

For example, a human restriction fragment length was determined by cDNA probe (B) and Hind III restriction endonuclease using the Southern blot technique (See FIG. 7). The two RFLP alleles detected are a fragment at 6.5 kb (allele) and a fragment at 3.5 kb (allele 2). Major constant fragment bands are seen at approximately 2 and 5 kb with minor constant bands at 0.9 and 7.5 kb. Allele 1 is present in approximately 30% of the X chromosomes of the Caucasian population. Allele 2 is present in approximately 20% of the X chromosomes of the Caucasian population. In FIG. 8 Lanes A, B and D, DNA from women who are homozygous for allele 1 is shown. In FIG. 8 Lane C, DNA from a woman who is heterozygous for both alleles 1 and 2 is shown. FIG. 8 Lane E contains DNA from a man that only possesses allele 2. This RFLP, and others determined by the clones we have isolated, will enable one to monitor the androgen receptor gene in various disease conditions described herein.

An example of using the androgen receptor clones to detect mutations is shown in FIG. 8 where five different complete androgen insensitive patients' DNA are digested with EcoRl, electrophoresed on a Southern blot, and probed with cDNA probe B. The patient in lane B lacks a 3 kb band indicating that part of the androgen receptor gene is deleted. Further analysis of this and other patients DNA is possible with other AR probes and by sequencing by standard methods and comparing the abnormal sequence to the normal sequence described herein.

Other potential uses for oligonucleotide sequences disclosed, for example in construction of therapeutics to block genetic expression, will be obvious to one of ordinary skill in the art.

What is claimed is:

1. An isolated or purified human androgen receptor protein produced by a cell transfected or transformed with a vector comprising the DNA sequence of FIG. 5.

2. An isolated or purified human androgen receptor protein produced by a cell transfected or transformed with a vector comprising the sequence of nucleotides 1864 to 4635 of FIG. 5.

3. A composition comprising a substantially pure protein produced by translation of the DNA sequence of FIG. 5.

* * * * *

UNITED STATES PATENT AND TRADEMARK OFFICE
CERTIFICATE OF CORRECTION

PATENT NO. : 6,307,030 B1
DATED : October 23, 2001
INVENTOR(S) : French et al.

It is certified that error appears in the above-identified patent and that said Letters Patent is hereby corrected as shown below:

Column 10,
Line 11 should read -- include chromosomal, non-chromosomal and synthetic --.

Signed and Sealed this

Fifteenth Day of November, 2005

JON W. DUDAS
*Director of the United States Patent and Trademark Office*